United States Patent [19]
Repke

[11] 3,938,522
[45] Feb. 17, 1976

[54] DISPOSABLE DIAPER

[75] Inventor: Virginia L. Repke, Oak Forest, Ill.

[73] Assignee: Johnson & Johnson, New Brunswick, N.J.

[22] Filed: Sept. 11, 1973

[21] Appl. No.: 396,242

Related U.S. Application Data

[63] Continuation-in-part of Ser. No. 266,013, June 26, 1972, abandoned, which is a continuation-in-part of Ser. No. 187,239, Oct. 7, 1971, abandoned.

[52] U.S. Cl. ............................. 128/287; 128/290 P
[51] Int. Cl.² ......................................... A61F 13/16
[58] Field of Search.... 128/287, 284, 290 R, 290 W

[56] References Cited
UNITED STATES PATENTS

| | | | |
|---|---|---|---|
| 2,788,063 | 4/1957 | Morin | 128/284 |
| 2,862,251 | 12/1958 | Kalwaites | 128/290 W |
| 2,890,700 | 6/1959 | Lonberg-Holm | 128/284 |
| 3,017,304 | 1/1962 | Burgeni | 128/290 R |
| 3,402,715 | 9/1968 | Liloia et al. | 128/287 |
| 3,612,055 | 10/1971 | Mesek et al. | 128/287 |
| 3,636,952 | 1/1972 | George | 128/287 |
| 3,663,348 | 5/1972 | May, Jr. et al. | 128/290 W |
| 3,692,622 | 9/1972 | Dunning | 161/124 |
| 3,726,750 | 4/1973 | Stillings | 161/57 |
| R26,151 | 1/1967 | Duncan et al. | 128/284 |

Primary Examiner—Richard A. Gaudet
Assistant Examiner—Henry S. Layton

[57] ABSTRACT

A disposable multi-layer diaper of high absorptive capacity is provided which comprises as a first layer, a porous facing web to be brought into contact with an infant's skin. A second layer, in juxtaposition to the facing layer, is a highly porous, loosely compacted cellulosic batt having greater wettability than that of the facing web. The batt is slightly narrower than the facing layer to provide exposed side portions of the facing layer outwardly of the side edges of the batt. A third layer, integral with the second, is a continuous, paper-like, densified, higly compacted layer of the same cellulosic material as the second layer but of substantially smaller average pore size. The third layer is thickened in selected areas to provide an increased volumetric flow capacity for rapidly drawing fluid away from an initially wetted area and directing it to areas of the densified layer remote from the wetted area. The thickened areas may be coherent and unitary, or may include substantially fiber-free voids surrounded by fibrous strata. The final layer is an impervious backing sheet that is substantially coextensive with the facing layer, and which is adhered to the densified layer over a widely distributed area of adhesion and to the side portions of the facing layer beyond the edges of the batt. Opposite sides of the diaper are folded inwardly about first fold lines inwardly of the side edges of the batt, and the folded side portions are folded outwardly about second fold lines outwardly of said first fold lines, but inwardly of the side edges of the batt, to thereby provide thickened zones at opposite sides of the batt that include three thicknesses of batt material.

39 Claims, 23 Drawing Figures

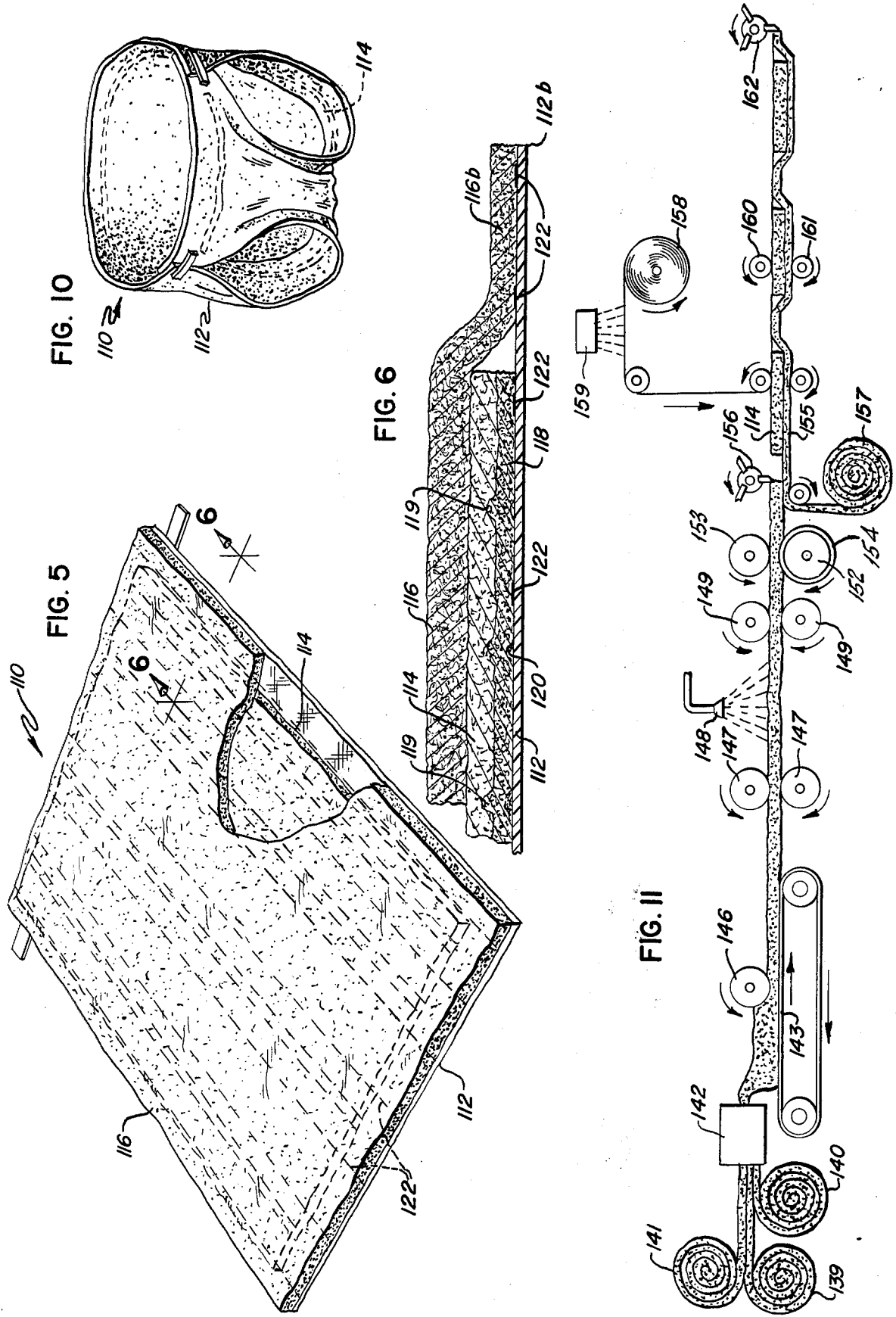

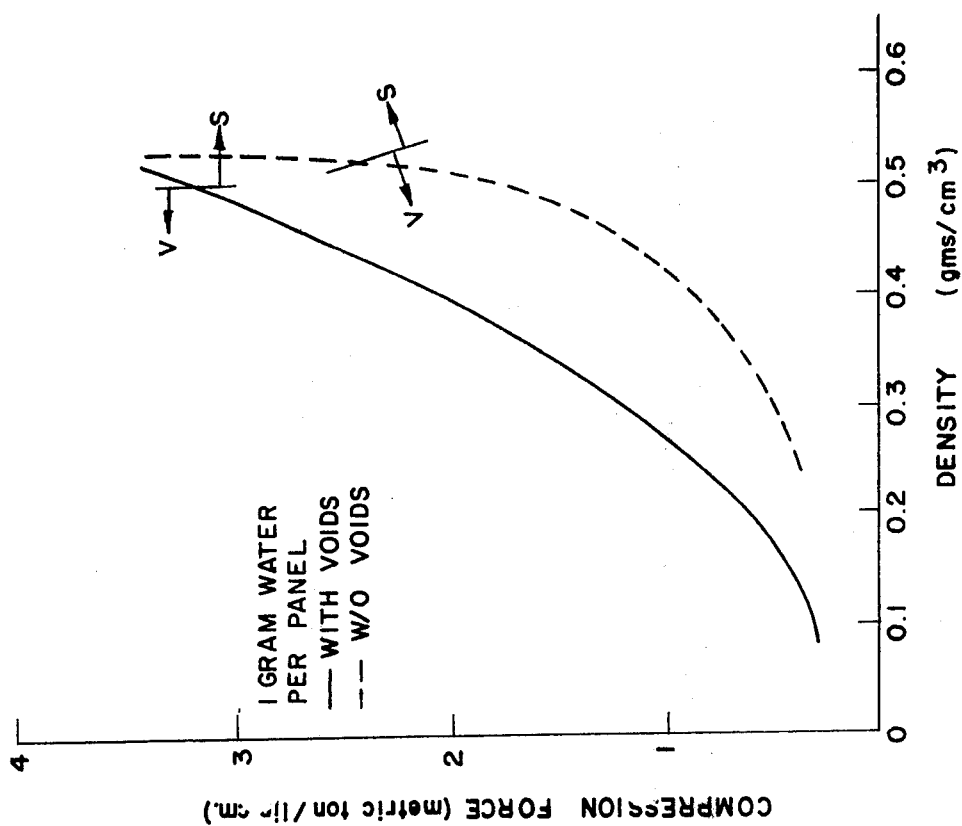
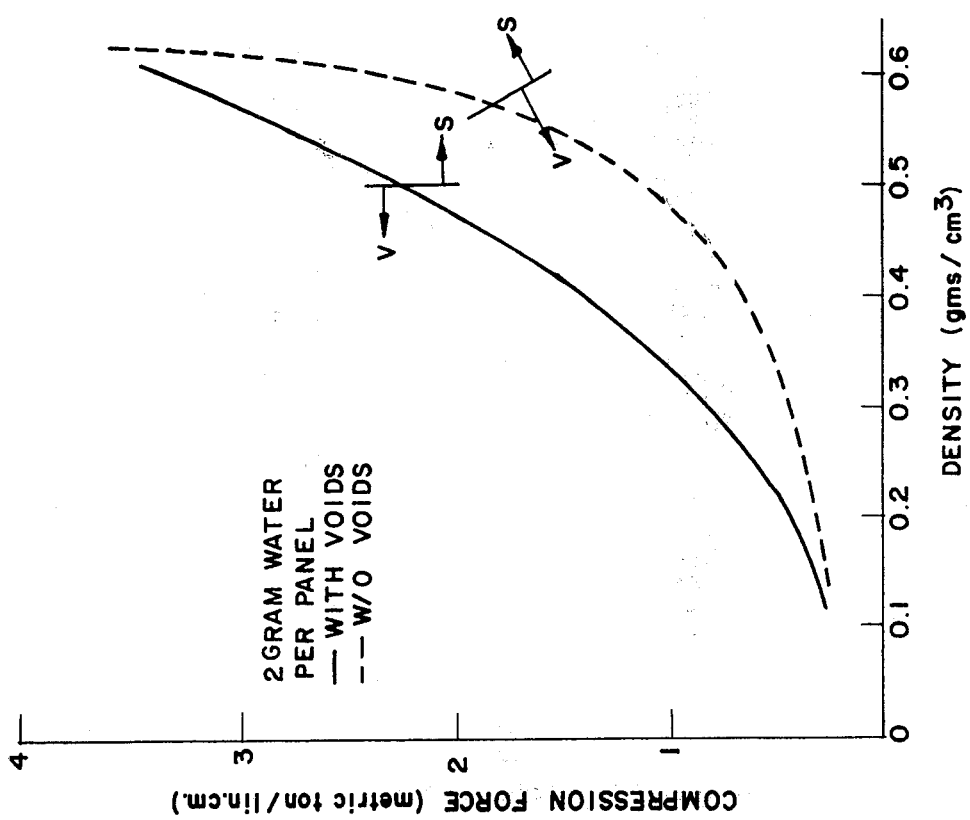

DISPOSABLE DIAPER

CROSS-REFERENCE TO RELATED APPLICATION

This application is a continuation-in-part application of my application Ser. No. 266,013, filed June 26, 1972, now abandoned which was a continuation-in-part of application Ser. No. 187,239, filed Oct. 7, 1971, and now abandoned.

BACKGROUND OF THE INVENTION

Disposable diapers have met with increased commercial acceptance in recent years primarily because of their convenience, as opposed to cloth diapers, which need to be laundered once soiled. Many different constructions have been proposed and used, and some have met with widespread commercial success in spite of certain inadequacies in functional properties.

One of the most serious prior art problems has been the inability to provide a suitable construction that would keep moisture away from the surface of the diaper which comes into contact with the infant's skin and thereby avoid skin irritation and infection. Commonly assigned Mesek et. al. U.S. Pat. No. 3,612,055 discloses several diaper constructions that function extremely well in keeping moisture away from an infant's skin, while at the same time handling a full volume discharge of urine.

These functions are accomplished by a multilayer diaper comprising, in order, a fibrous facing layer which is to be brought into contact with the infant's skin, a layer of highly porous, loosely compacted cellulosic batt, a paper-like densified, highly compacted cellulosic fibrous layer integral with the loosely compacted batt and an impervious backing sheet adhered to the densified layer throughout the interface therebetween. The facing layer is of porous construction and its fibers have less wettability for water than the fibers of the loosely compacted batt, resulting in a tendency for liquid to flow from the facing web into the batt. The densified fibrous layer has a smaller average pore size than the loosely compacted batt, resulting in a tendency for liquid to flow preferentially from the batt into the underlying densified layer rather than to other areas of the batt, thus tending to restrict wetting in the batt to an area of moderate size. Liquid flowing into the densified layer tends to spread laterally because of its wicking action and liquid which might pass through the densified layer during discharge (when flow is rapid) is held back by the impervious backing sheet for sufficient time to permit absorption to take place. Liquid in excess of the absorptive capacity of the densified layer is forced back by the impervious layer into the dry portion of the loosely compacted batt, thus utilizing the additional absorptive capacity therein.

The above-mentioned patent discloses basically two different types of absorbent panels, viz., those wherein the paper-like, densified layer extends continuously over a given area of the loosely compacted batt, and those wherein the paper-like densified layer is discontinuous and arranged in a preselected geometric pattern. The advantage of the absorbent structures within the latter group is the ability to provide directionalized fluid flow, i.e., the fluid tends to flow in the direction of the densified portions, as opposed to flowing into the loosely compacted portions of the absorbent panel. Thus, by utilizing an absorbent panel wherein the spaced densified portions extend in a lengthwise direction, the fluid flows preferentially along the densified portions to spread out longitudinally within the densified layer before spreading laterally and striking through at the side edges thereof. While absorbent panels having spaced densified portions provide increased ability to control and direct the flow of fluid, as opposed to a continuous paper-like, densified layer wherein the fluid flow is substantially equal in all directions, such structures have a reduced volumetric fluid storage capacity in the densified portions and somewhat reduced overall structural integrity, as compared to comparable structures having a continuous paper-like densified layer. Furthermore, because the spaced densified portions of the panel are separated by loosely compacted batt portions having limited wickability, the linear flow rate in the densified portions is far greater than the rate of lateral spread, with the result that fluid often reaches the ends of the densified portions before it spreads outwardly into previously unwet portions of the absorbent structure. This, of course, can result in fluid leakage at the ends of the absorbent panel.

In absorbent panels including a continuous densified layer of uniform thickness, because of the equal flow rate in all directions, it is possible for fluid to migrate to the side edges of the densified layer before it reaches the longitudinal edges thereof, with resultant fluid leakage at the sides of the product. Thus, both types of absorbent panels disclosed in the above mentioned patent have certain limitations.

The above-mentioned patent also discloses an arrangement which provides for improved sealing adjacent the thighs of an infant. To this end, the patent teaches that the facing layer may be wider than the backing sheet, with the edges of the facing layer being folded inwardly to make the facing layer substantially coextensive in size with the backing sheet and to provide increased thickness at the marginal side portions of the diaper. This latter construction not only provides for improved sealing, but also enhances the balance and feel of the diaper.

While diapers with the facing layer folded in the manner described above have functioned satisfactorily to produce the desired results, since the facing layer is the most costly component of the diaper, the improved sealing effect and improved feel have been obtained as a result of an increased amount of facing layer material, beyond that which otherwise would be required, and this has resulted in an increase in the cost of manufacturing the product, a matter of no small importance in a disposable diaper.

SUMMARY OF THE INVENTION

The present invention represents a significant improvement upon diaper structures as disclosed in the above-mentioned patent, by providing an absorbent panel that includes a highly porous, loosely compacted fibrous cellulosic batt with an integral, continuous paper-like, densified, cellulosic fibrous layer which, in selected areas, is thickened with additional densified cellulosic fibrous material. The thickened and unthickened portions of the densified layer portion of the absorbent panel cooperate with one another to provide for increased flow of fluid within the densified portions of the absorbent structure by reason of a greater cross sectional area therewithin, thereby tending to cause a greater amount of the fluid passing through the facing layer and striking the loosely compacted batt portion of the absorbent panel to flow preferentially into the densified layer portion and then throughout the densified layer portion toward its outer edges.

The spaced thickened portions of the densified layer provide a mechanism which enables an increased volume of fluid to flow in the densified layer (as compared to the unthickened portions of the densified layer), and this fluid is rapidly transported into remote areas of the densified layer portion before it flows back into the loosely compacted fibrous batt portion of the absorbent panel. The thickened densified portions thereby make possible the utilization of substantially the entire absorbent capacity of the densified layer portion, i.e., the fluid is transported to both the side and longitudinal edges of the batt portion of the absorbent structure, before the fluid flows back into the loosely compacted batt portion of the absorbent structure.

The unthickened portions of the densified layer portion function as bridging regions which transport fluid from one thickened densified portion to another at a relatively rapid rate, although the volume of fluid that spreads from one thickened portion to another is less than the volume of fluid that is transported along the thickened portions themselves in a given period of time. However, as the spreading fluid reaches unwetted thickened densified portions, the increased volumetric flow capacity resulting from these thickened portions provides a means for rapidly taking up the fluid and causing it to spread out rapidly along the thickened portions and into previously unwet densified layer portions of the absorbent panel. Thus, by virtue of having a continuous paper-like densified portion with selectively thickened regions therein, a medium is provided for preferentially drawing fluid away from the loosely compacted batt of the absorbent panel, while enabling the fluid to spread outwardly in the entire densified layer at a relatively rapid rate by virtue of the increased flow rate along the thickened portions as well as from one thickened portion of the densified layer to another.

In one embodiment of the invention, the thickened portions of the densified layer are provided by spaced, parallel strips or lines of densified fibrous material that extend lengthwise of the structure. When the absorbent panel is wetted in the central region of the batt portion and the fluid flows into the densified layer of the absorbent panel, the thickened portions in that region function to rapidly transport the fluid lengthwise of the structure away from the initially wetted region, while the densified bridging portions between the thickened portions cause the fluid to spread laterally outwardly at a rapid rate, thus causing the fluid to encounter additional thickened portions of densified material, with resulting increased longitudinal flow. It will be appreciated with the above described type of structure, an arrangement is provided that will rapidly draw fluid away from an initially wetted region, and cause it to spread out and utilize the absorptive capacity of the entire densified layer portion prior to its flow back into the loosely compacted batt of the absorbent panel.

The above-mentioned densified strips or lines need not be continuous to provide the improved fluid directing function, and it has been found that lines formed of relatively closely spaced strips or sections have also functioned satisfactorily. Indeed, with this latter arrangement an extremely conformable and comfortable diaper is produced, which at the same time retains the desired fluid directing characteristics.

The cross-sectional area of the paper-like densified layer of absorbent panels that includes the thickened portions is greater than the cross-sectional area of a continuous paper-like densified layer with no thickened portions, or a discontinuous layer formed of spaced densified zones, with the result that an increased volumetric storage capacity is provided within the smaller capillary area densified layer portion of the present invention.

In the embodiment described above, the unthickened portion of the densified layer merges with the loosely compacted batt portion of the absorbent panel at a generally planar interface. The thickened portions of the densified layer extend beyond the said interface and into the interior of the batt portion to provide a three dimensional stregthening effect which markedly improves the structural integrity of the absorbent product. The increased strength imparted to the absorbent panel of the diaper is important not only in use when the structure resists the stress imposed by the absorbed liquid, but it is also of significance during the manufacture of the diaper, since it improves the handling capabilities enabling the diaper to be produced without difficulty by high speed machinery.

Furthermore, since the thickened densified portions extend into the batt portion of the absorbent panel, they are positioned closer to the facing layer and will be struck by fluid more quickly than the fluid would reach a densified layer of uniform thickness. As a result, the spread of fluid is initiated more quickly. The thickened densified portions may extend through the entire cross-sectional thickness of the batt, which gives the batt a marked increase in structural integrity. With this latter structure, sufficient stability is imparted to the batt to permit the use of lower densities in the loosely compacted portion thereof than heretofore thought possible. This, of course, enhances the drape and handle of the diaper, and makes it more comfortable to the infant. Thus, the diaper of the present invention has all of the advantages of the diaper structures disclosed in the above-mentioned patent, while having improved strength, increased fluid storage capacity, and improved fluid directing and absorbing properties.

Depending upon the amount of moisture applied and the degree of compaction, the thickened portions may be coherent and unitary, i.e. any zone within the thickened portion has a density greater than the density of the remainder of the absorbent product above the densified layer; or the thickened portions may include densified fibrous strata which surround pores or voids that are essentially free of fibers and which have a density that is substantially zero, and in any case substantially less than the density of the remainder of the absorbent product above the continuous densified layer. This latter type of densified structure provides an increased volumetric stroage capacity and an increased volumetric carrying capacity as compared to cohesive or unitary thickened portions containing the same total amount of fibers.

The diaper of the present invention also provides a means for increasing the sealing efficiency between the sides of the diaper and an infant's thighs, without substantially increasing the cost of the product and withou sacrificing any of the structural and functional advantages mentioned above. To this end, the batt layer of the diaper of the present invention is widened to an extent that it is only slightly narrower than the facing layer and backing sheet, so that when the side portions of the diaper are folded in the conventional manner, i.e., inwardly about a first fold line and outwardly about a second fold line, three thicknesses of batt material are provided at the side margins of the diaper. The batt layer, adding its thickness to that of the facing layer near the edge thereof, provides an efficient sealing mechanism around the thighs of an infant, and since the batt layer is composed entirely of inexpensive paper-making fibers, the improved sealing efficiency is provided with little or no increase in cost of the diaper. In this regard, for a desired volumetric storage capacity, a batt of predetermined thickness and width comprised of a given number of fibers was provided heretofore; and following the teachings of the present invention, the same volumetric storage capacity can be provided in a batt with the same overall density by utilizing the same number of fibers and making the batt slightly thinner. The wider and thinner batt also makes the diaper more comformable and easy to handle.

The batt portion of the diaper of the present invention may also be heavier, i.e., more dense, in the central region than at the side marginal edges to concentrate a large volume of fluid in the central region and thereby minimize leakage at the sides of the diaper. In this embodiment, when the batt is of a given absorptive capacity and has a given number of fibers, making the central region heavier inherently makes the side portions lighter than would be obtained in a batt or uniform density and thickness. The central region of the batt portion is preferably thicker than the side marginal edges thereof, and the relatively thin, low density side marginal edges enable the diaper to be wrapped into close conformity with the infant's thighs with a minimum of wrinkling. As a result, any tendency for skin irritation is minimized, even after the diaper has been worn for a prolonged period. Furthermore, fluid leakage from a saturated diaper is more effectively prevented, thus minimizing soilage of outer garments and bedding.

By virtue of increasing the width of the batt layer, the overall strength of the diaper is also significantly increased, since the densified portion of the batt layer provides an increased area that is available for adhering to the backing sheet. Moreover, since the entire batt layer is slightly thinner, the densified and selectively thickened integral portions add significantly to the strength of the batt itself, particularly when the thickened portions extend through a significant portion of the cross-sectional thickness of the batt.

The increased area of densified layer also provides for enhanced lateral and longitudinal liquid spread, as described above. Although the densified layer is closer to the side margins of the diaper than in previously known embodiments, there is nevertheless sufficient extension of the less wettable facing layer beyond the outer edges of the batt to effectively obstruct migration of fluid beyond the side edges of the diaper. In fact, the narrower side margins in the present diaper of facing fabric width over width of the batt is more than compensated for by the factors of batt construction (discussed above) tending to hold liquid in the central portion of the batt; and simulated use tests with weighted dolls have indicated that there is actually less tendency for marginal leakage in the diaper of this invention than in the prior diaper with the thicker, narrower batt.

The diaper with improved sealing, handle and feel characteristics may be provided without significant modifications to the equipment that has been utilized to manufacture diapers of the type disclosed in the above-mentioned patent. For example, to obtain the wider and thinner batt it is necessary only to grind a wider pulpboard, and to obtain the wider and thinner batt having a thickened central region it is necessary only to simultaneously grind one or more further pulpboards narrower than the wider pulpboard and centered with respect thereto. Since overall width of the diaper of the present invention is the same as that disclosed in the above-mentioned patent, the same apparatus that has been used in the past to effect the folding of the sides of the diaper can be utilized to fold the diaper of the present invention. Therefore, the cost of manufacturing the diaper having, when folded, three thicknesses of batt material at its side portions is not increased.

The apparatus for producing the selectively thickened densified layer of the batt portion may include spaced calander rolls for applying pressure to a fibrous web after it has been moistened to form a continuous densified layer on one side of the web, and a ribbed embossing roll which cooperates with a back up roll to form the thickened portions of the densified layer. In a diaper wherein the thickened densified portions of the batt extend completely through the cross-sectional thickness of the batt, the ribs on the embossing roll are spaced in close proximity to the periphery of the back up roll, and when the entire central region of the batt is thickened, the ribs in the center of the embossing roll may have a smaller outer diameter than the ribs at the outer portions of the roll. When the continuous densified layer is formed on the batt having the thickened central region, it is preferred to use cylindrical calendering rolls, since this results in the application of greater pressure to the central region of the batt to form a densified layer which is thickened throughout this area (in addition to the localized thickening derived from the embossing roll). The diaper which includes a batt having a continuous densified layer that is thickened throughout its center functions in an improved manner, as compared to a batt having a continuous densified layer of equal thickness, since the diaper is usually initially wetted in the central area, and the increased thickness of the densified layer provides a vehicle for more rapidly transporting a larger volume of fluid from the initially wetted area. The further thickened densified lines in the thickened central region of the continuous densified layer provide a still further means for directing fluid to remote areas of the densified layer. The thickened central portion of the continuous densified layer also increases the volumetric storage capacity of the densified layer, so that a larger volume of fluid can be retained in spaced relationship with respect to the facing layer of the diaper.

BRIEF DESCRIPTION OF THE DRAWINGS

FIG. 5 is a perspective view, similar to FIG. 1, and illustrating a modified diaper structure;

FIG. 6 is an enlarged partial cross section of the diaper of FIG. 5 taken along plane 6—6;

FIG. 10 is a perspective view on a reduced scale of the diaper of FIG. 5 in its configuration after being put on an infant;

FIG. 11 is a simplified schematic view of the production line in which the diaper is made;

FIGS. 18–21 are graphs showing the relationship between compression force and density at various moisture add-on levels in connection with the embodiment illustrated in FIGS. 15 and 16.

DESCRIPTION OF THE PREFERRED EMBODIMENTS

Figure 1:
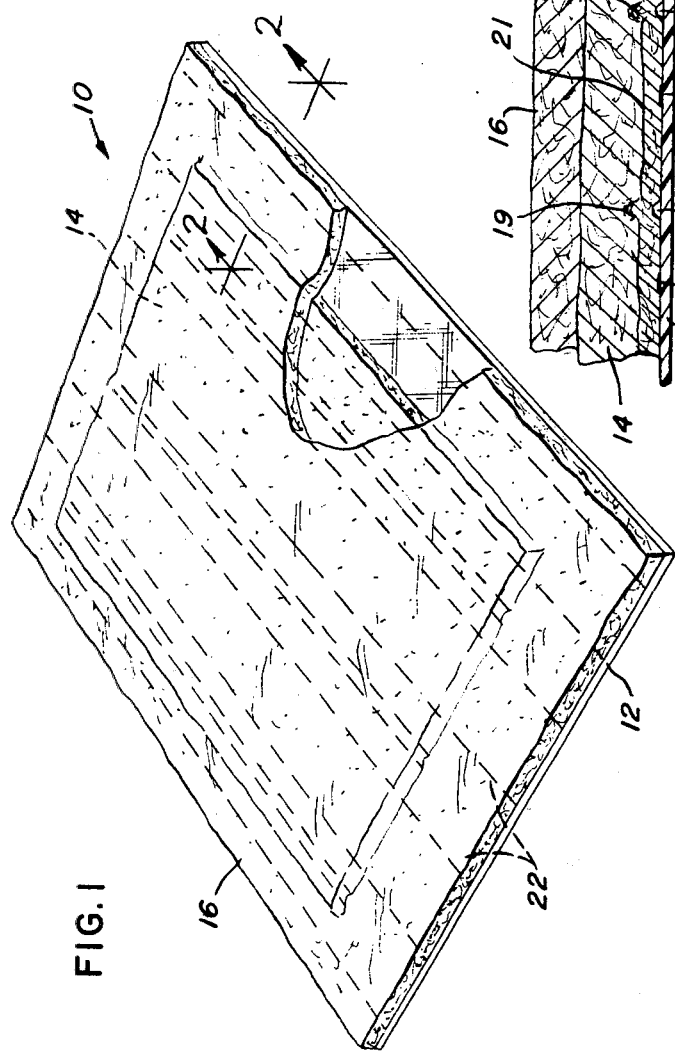
FIG. 1 is a perspective view, with certain portions broken away, of an open unfolded diaper.

While this invention is susceptible of embodiment in many different forms, there is shown in the drawings and will herein be described in detail preferred embodiments of the invention and modifications thereof, with the understanding that the present disclosure is to be considered as an exemplification of the principles of the invention and is not intended to limit the invention to the embodiments illustrated. The scope of the invention will be pointed out in the appended claims.

Figure 2:
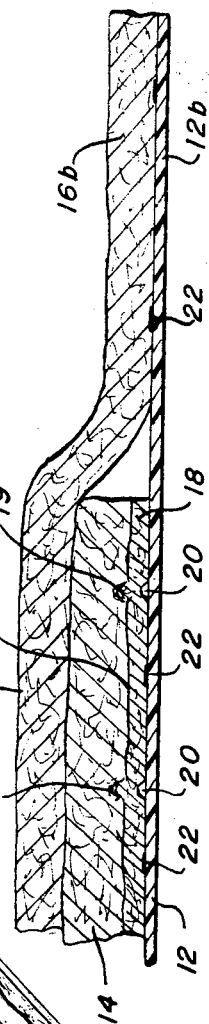
FIG. 2 is an enlarged partial cross section of the diaper of FIG. 1 taken along plane 2—2, illustrating the internal configuration structure.

Referring to the drawings, and particularly to FIGS. 1 and 2, the diaper assembly 10, when fully opened and laid out flat, comprises a lowermost water-impervious sheet 12 which is rectangular in shape, a highly water-absorbent fibrous pad, or batt 14, which is also rectangular in shape, but smaller than the impervious sheet and centrally disposed thereon, and an overlying facing layer 16 of fibrous material, which is also rectangular in shape, equal in dimension, and coterminous with the impervious sheet and in contact therewith in the marginal portions of the diaper extending peripherally beyond the absorbent pad, i.e., in the portions 16b and 12b of facing layer 16 and impervious sheet 12, respectively. The batt 14 has a continuous paperlike densified highly compacted lowermost fibrous layer 18 that includes spaced, parallel thickened densified portions 19. Densified layer 18 is adhered to the impervious sheet by bead lines of adhesive 22 substantially throughout the interface therebetween. Marginal portions 16b and 12b are also adhered to each other by bead lines 22.

In the preferred embodiment of the invention, moisture impervious sheet 12 is formed of polyethylene having a thickness of approximately 0.001 inch. The sheet may be smooth, or may be embossed to improve its drape and feel. Other suitable flexible moisture impervious sheets may be used in accordance with the invention, such as, for example, polyethylene terephthalate sheets having a thickness of about 0.0005 inch.

Batt 14 is formed of loosely compacted short cellulose fibers, such as wood pulp fibers, or cotton linters, or mixtures thereof, which are primarily held together by interfiber bonds requiring no added adhesive, as is known in the art. Briefly, this batt is a low bulk density coherent web of loosely compacted cellulose fibers preferably comminuted wood pulp fibers in the form of so-called "fluff".

The term "short fibers," as used herein, refers to fibers less than about one-fourth inch in length, in contrast to "long fibers," or "textile length fibers" which are longer than about one-fourth inch in length, and generally are between about ½ and 2½ inches in length. The former are substantially less costly than the latter. The classification of fibers by length may be carried out by the Clark Classification procedure described in the test manual of the Technical Association of Pulp and Paper Industry (TAPPI-T233 SU64).

The paper-like densified layer 18 of batt 14 is formed by a slight moistening of one surface of the batt followed by the application of pressure thereto. The nature of the batt and of its densified layer and the method of producing the same are described in U.S. Pat. No. 3,017,304, dated Jan. 16, 1962. The thickened densified portions 19 are formed by further compression of batt 14 while it is still moist, as will hereinafter appear.

The composite density of batt 14, including its densified layer 18, should be above about 0.07 gm./cc. and preferabbly between about 0.10 and 0.15 gm./cc. The foregoing density values are applicable to the diaper as produced. In storage and handling, the loft or thickness of the batt is increased to some extent, resulting in lowered densities.

Figure 3:
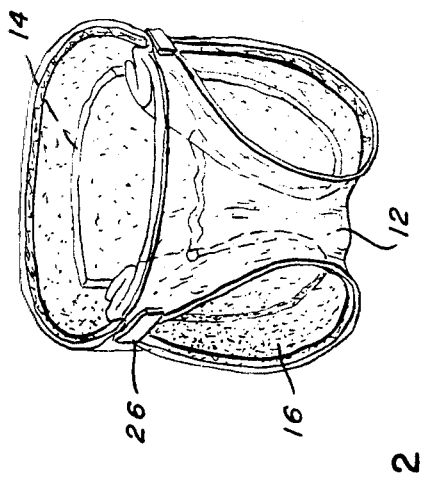
FIG. 3 is a perspective view on a reduced scale of the diaper in its configuration after being put on the infant.

In the embodiment of FIGS. 1–3 facing layer 16 is made up of a mixture of fibers consisting predominantly of short cellulosic fibers such as wood pulp fibers or cotton linters, in amounts of about 75% to about 98%, the balance being textile length fibers such as rayon. Short cellulosic fibers such as wood pulp fibers or cotton linters are substantially less expensive than textile length cellulosic fibers such as cotton and rayon, and this low cost is a factor in reducing the cost of the facing layer component of the diaper of this invention.

In the facing layer, the short fibers are in uniform admixture with 2% by weight of textile length fibers, such as 1.5 denier rayon fibers uniformly cut to 1½ inch length. The short and long fibers are randomly and substantially uniformly dispersed and bonded with a bonding agent such as a self-cross-linking acrylic emulsion. THe facing web is also treated with a wetting agent to partially counteract the water-repellency of the bonding agent and bring the facing layer to the desired degree of wettability. Facing layers of this character are described in greater detail in commonly-owned United States patent application Ser. No.

729,784, now U.S. Pat. No. 3,663,348.

Facing layers suitable for use in this invention have fabric weights in the range of 1 to 5 oz./yd.² and densities less than 0.15 gm./cc., generally in the range between 0.05 and 0.1 gm./cc. The dry strength of the facing layer, for a fabric having a weight of about 1.5 oz/yd.², is at least 0.15 lbs/in. of width in the machine direction and at least 0.10 lbs/in. of width in the cross direction. The fabrics have unusually good elongation, loft, softness and drape characteristics in comparison to prior products incorporating any substantial amount of short fibers.

An important aspect of this invention is the provision for selective wettability among the above-described fibrous components of the diaper, such that the moisture is selectively drawn from the facing layer into the body of the batt and then from the body of the batt into the densified layer thereof.

The least wettable of the fibrous elements of the diaper of this invention is facing layer 16. However, even in the facing layer the ability to be wetted by water is desired. Water repellency in the facing layer is not desired since, at the desired fiber densities in the facing layer, water repellency can prevent the liquid from penetrating into the facing layer and the absorbent layers behind it, just as a tent fabric holds back penetration of rain water. For this reason, the facing layer is usually treated with a wetting agent, such as an anionic surfactant, to moderate and reduce the water repellency which may be imparted to the short and long fibers of the web by the bonding agent which bonds them into an integral layer. After treatment with a wetting agent, the facing layer is receptive to penetration by urine but remains less wettable than the batt.

The body of batt 14 is substantially more wettable than the facing layer and tends to draw liquid away from the facing layer. The individual fibers of the batt are extremely wettable, generally having liquid-fiber contact angles below about 15° and approaching zero in the optimum embodiment, as described in detail in the above-mentioned application. The wickability, or preferential absorptivity of the body of the batt for water is limited, however, by its low density which results in a large effective capillary radius for the capillaries between adjacent fibers.

The pressure causing a liquid to enter a cylindrical capillary is expressed by the equation:

$$P = \frac{2\gamma \cos \theta}{r}$$

wherein

P is the capillary pressure,
$\gamma$ is the surface tension of the liquid,
$\theta$ is the liquid-fiber contact angle, and
r is the capillary radius.

With a given liquid, the pressure (capillary force) increases with the cosine of the liquid-fiber contact angle (reaching a maximum where the angle is zero), and decreases with narrower capillary radii so that narrower capillaries will draw liquid from wider ones.

The relative wickability between facing layer 16 and the body of batt 14 is affected by both the relative densities of the layers and the relative wettability of the individual fibers in each layer. The facing layer is sometimes more dense than the body of the batt, tending to provide greater wickability in the facing layer, but even then the individual fibers of the batt have substantially smaller liquid-fiber contact angles than those of the facing layer, overcoming the density difference and providing a substantial overall increase in capillary pressure to absorb liquid into the body of the batt.

Densified fiber layer 18 of the batt provides the maximum capillary pressure because it combines the very low contact angle of the fibers of the batt with the high density (small capillary radius) of the densified fibers.

When urine is voided into an area in facing layer 16, it partially wets the facing layer and is absorbed therein, spreading out to a limited extent to form a roughly circular wetted zone therein. When the urine passes through the facing layer and comes into contact with the body of batt 14, it is preferentially absorbed into the body of the batt because of the enhanced wettability thereof. It spreads within the body of the batt to wet a roughly circular zone therein that is slightly larger than the wetted zone in facing layer 16. When the urine passes through the body of the batt it initially contacts one or more of the thickened densified portions 19 and the urine is strongly drawn into the densified layer 18 because of its high density and is spread laterally through a much larger zone, or to the edges of the batt, depending on the amount of urine passed. The urine is transported rapidly along lines 19, more rapidly than it is transported transversely across the densified bridging portions between the lines, with the result that the roughly circular zone in the initially wetted loosely compacted portion of the batt is distorted into a roughly oval zone in the densified portion of the batt.

The urine is transported relatively rapidly in all directions of the densified layer 18 because the densified layer is continuous over one face of the absorbent panel. However, the thickened portions 19 provide for an increased volumetric flow rate in the longitudinal direction to rapidly move a larger volume toward the ends of the absorbent structure. The bridging portions provided by the portions of the densified layer between the thickened portions rapidly transport the liquid away from the initially wetted area of the densified layer and into contact with previously unwetted thickened portions, with the result that liquid is rapidly drawn away from the initially wetted area and transported both longitudinally and transversely into substantially all portions of the densified layer.

On occasions when a substantial amount of urine has been voided, the densified layer becomes saturated and excess urine, aided by the presence of impervious sheet 12 and its adherence to the densified layer in a discontinuous pattern substantially throughout the interface therebetween, flows into the previously dry portions of the body of the batt, and finally into the previously dry portions of the facing layer. It is to be noted, however, that such flow from a saturated densified layer is from the outermost portions of the diaper inward so that most of the facing layer remains dry until all other fibrous portions of the diaper are saturated. The thickened densified portions provide for an increased cross-sectional area in the absorbent panel, as compared to a densified layer of uniform thickness or a plurality of spaced densified zones, with the greater cross-sectional area providing a capacity to abbsorb an increased volume of urine. Thus, with the structure of the present invention more urine can be stored in the densified layer, and the tendency for urine to flow back into the batt or into the facing layer is resisted.

The densified layer of the batt, for the reasons explained above, creates a high capillary pressure which tends to move liquid away rapidly from the area of the original wetting. However, the speed of liquid migration is limited in the densified layer because of the resistance provided by its small capillaries. The composite batt used in this invention, with its densified layer in intimate contact with absorbent material of lesser density, provides improved speed of liquid migration over either the densified layer alone, or the uncompressed layer alone.

While it is not desired to be bound by any particular therory of operation, it is believed that the improvement in speed of liquid migration obtained by the cooperation of the dense and uncompressed layers of the batts used in this invention results from the proximity of the two layers and the fact that just adjacent to the high capillary pressure generated by the dense layer are the large capillaries of the uncompressed layer which can move larger quantities of the liquid with relatively little flow resistance.

There is also cooperation between the densified layer of the batt and impervious sheet 12 to which it is adhered. A voiding of urine usually takes place within a short time, and the rate of absorption of the diaper might be overwhelmed during this short period in spite of the diaper's ultimate capacity to absorb the amount of liquid voided and in spite of the relatively high rate of absorption obtainable for the reasons specified above. The impervious sheet serves to hold the urine and keep it from wetting the bed clothes or outer clothing so that the absorptive portions of the diaper can have the time to function. In addition, the impervious sheet serves as an anchor to stabilize the fluff portion of the batt against migration of the loosely compacted fibers, since the impervious sheet is adhered to the densified layer integral with the fluff portion of the batt, over a widely distributed area.

It is to be noted that the facing layer as assembled into the diaper is coterminous with the impervious sheet and there is no folding over of the impervious sheet to envelope any edge of fibrous material. Thus, there is no portion of the upper surface of the diaper which is covered with any plastic material, and no plastic material comes into direct contact with the infant's skin when the diaper is affixed in position by pins or tabs. Prolonged direct contact of plastic material with an infant's skin can cause irritation and infection but, nonetheless, is employed in prior art disposable diapers to provide an impervious seal to the infant's skin. The superior absorptive capacity of the diaper of this invention and its superior functioning make such plastic-to-skin contact unnecessary.

The diaper of this invention is normally packaged and sold in a folded condition as described in the abovementioned patent. Briefly, the side margins 12b and 16b of the impervious sheet 12 and the facing web 16, together with a portion of batt 14, are folded inwardly in a first fold to provide as the uppermost layer of the fold, a portion of the moisture impervious sheet. This sub-assembly is then folded outwardly along each edge in a second fold to cover the first folded portion and to expose the edge portion of the facing web as the upper layer of the double fold. In the preferred embodiment, each double fold at the edge of the diaper comprises approximately one-third of the resulting transverse dimension of the folded diaper, leaving approximately one-third of the width of the folded diaper as a central unfolded and uncovered portion.

Figure 4:
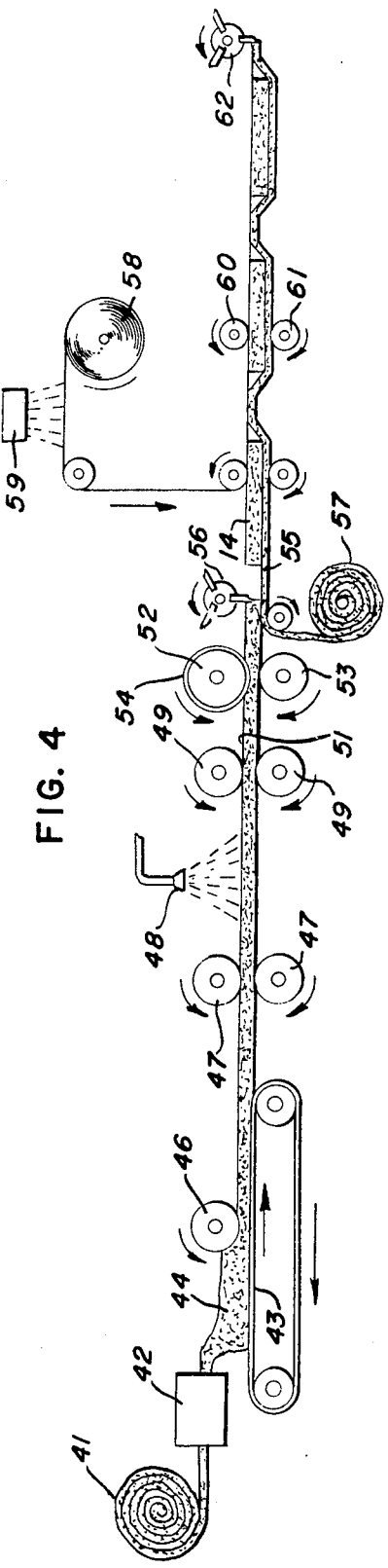
FIG. 4 is a simplified schematic view of the production line on which the diaper is made.

The diaper is held in its folded condition by two small central spots of adhesive applied between the main body of the diaper and the overlying sides 16b of the facing web, one spot on each folded side of the diaper. When the diaper is to be put on the infant, the folds are opened on one side of each of the adhesive spots, and the open portion of the diaper is put under the infant's buttocks while the folded portion is raised into the crotch region. The final form of the diaper is shown in perspective on a reduced scale in FIG. 4. In one form of the invention, as illustrated in FIG. 4, the diaper is provided with adhesive tabs 26, each having a fixed end secured to the imprevious sheet 12 and a free end wherein the adhesive surface is covered with a facing sheet. The facing sheets are removed to expose the adhesive surfaces when the diaper is applied to the infant, as in the configuration shown in FIG. 4, and the free ends of the adhesive tabs are secured to opposite corners of the diaper.

Suitable fibrous structures for making the pads or batts 14 used in this invention are made from short cellulosic fibers obtained by the grinding or comminution of compacted wood pulp fibers or cotton linters. In the embodiment of FIGS. 1–3 where the thickened densified portions 19 extend only partially through the cross-sectional thickness of the batt 14, the compacted cellulosic material is preferably at a moisture content of 5–10 weight percent (or is slightly moistened to bring it to that range) before being subjected to the grinding operation so that the fibers produced by grinding have sufficient moisture to have the capability of developing weak interfiber hydrogen bonds which give some coherence to the body of the batt. As will hereinafter be described in connection with the embodiments of FIGS. 7–10, when the thickened densified portions extend through a substantial portion of the cross-sectional thickness of batt 14, or completely through the cross-sectional thickness to the side of the batt opposite the side having the continuous densified portion, the batt is strengthened to an extent that the amount of moisture added to the cellulosic material can be reduced, or eliminated entirely.

The batts are initially formed by air blowing the slightly moist cellulosic fibers onto a support at a total weight of about 2 to about 10 oz/yd.$^2$, and then subjecting the air blown fibers to heavy compression. The small amount of moisture which may, when required, be added to cellulosic pulpboard is uniformly distributed throughout the air blown fibers by the grinding and air blowing operations, and after compression, this moisture provides weak hydrogen bonding to give some integrity to the body of the batt.

The dense compacted paper-like layer or skin is prepared by moistening a surface of the cellulosic batt with a fine spray of water, and then subjecting the moistened batt to pressure. The formation of the densified skin on the cellulosic batt is believed to be due to the formation of strong hydrogen bonds between contacting moistened fibers, similar to the bonds between the fibers in paper. By the proper selection of the amount of moisture applied to the surface of the batt and by the proper selection of degree of compression imposed, the properties of the densified skin may be varied as desired. The thickness, density, strength and other characteristics of the densified skin will depend upon the uniformity by which the moisture is applied, the depth to which it penetrates, and the degree to which the fibers are compressed. For example, by finely spraying about 0.0015 cc. of water per square centimeter of web surface and then exposing the web to a pressure of about 40 pounds per square inch, a suitable densified, coherent paper-like skin 18 is obtained on the surface of the web which has been moistened. The thickened densified portions 19 may be obtained by subjecting the web to additional pressure, as by the use of an embossing roll, while the web is still moist, and the additional pressure is preferably several times higher than the pressure that is applied to form the densified layer 18.

The short fibers used in making batt 14 of this invention are generally entirely fibers of wood pulp or cotton linters. HOwever, other cellulosic fibers may be used as well as blends of cellulose fibers with other fibers such as silk, wool, nylon and cellulose acetate. Highly purified kraft paper pulp fibers have proven to be most satisfactory for most applications.

The diaper of this invention may be assembled in equipment such as that schematically shown in FIG. 3. A roll of compacted wood pulp 41 is provided to feed a source of short cellulosic fibers to grinding mill 42 from which a stream of fibers is blown onto belt 43 as a layer 44 weighing between about 2 and about 10 oz/.yd.$^2$ The pulpboard normally has a moisture content of 5 to 10 weight percent, but if it is lower (as from prolonged exposure to a dry atmosphere) in producing the diaper of FIGS. 1–3 the pulpboard may be slightly moistened before grinding in mill 42 to bring its moisture content within the desired range.

Mill 42 grinds the pulpboard into individual short fibers. However, in one preferred embodiment, some of the pulpboard fibers are not completely comminuted and remain joined to other fibers in small clumps, generally smaller than about one-fourth inch across. It has been found that the presence of such small clumps of fibers in the body of batt 14 provides islands of increased tenacity for holding liquid. When an infant's weight on one portion of the batt densifies that portion and tends to concentrate the liquid in the densified portion, the presence of clumps of fibers elsewhere in the batt tends to hold the liquid in place. Preferably from about 2 to about 10 weight percent of the fibers should be in the form of such clumps. The importance of the clumps diminishes as the height of thickened densified portions 19 increases, and the percent of fibers in the form of clumps may be at the low end of the above mentioned range when the thickened densified portions 19 extend substantially, or completely, through the cross-sectional thickness of the batt.

The air blown layer is passed under compacting roll 46 from which it emerges with enough integrity to sustain itself as a web without the support of belt 43. The web then passes through a pair of calender rolls 47 for further compression and then under nozzle 48 which deposits a fine spray of moisture on the upper surface of the web. The moistened web then passes between another set of calender rolls 49 which exert heavy pressure on it to form a skin 51 on its upper surface.

The amount of moisture applied to the web may vary suitably from about 0.0005 to about 0.03 cc. of water per square centimeter of web surface, depending on the thickness of the paper-like densified skin desired, with lesser amounts of moisture being used for thinner webs and very thin, papery skins and greater amounts for thicker webs and skins of greater thickness.

The amount of pressure applied by rolls 49 may vary from about 5 to about 100 or more pounds per square inch, with the commercially preferable range being from about 10 to about 50 pounds per square inch. In a typical embodiment, the web is sprayed with about 0.0015 cc. of water per square centimeter of web surface and subjected to a pressure of about 40 pounds per square inch to obtain a densified, coherent papery skin of uniform thickness on the surface of the web which has been moistened. The amount of moisture is selected so that the web is still moist following formation of the skin 51. The web then passes between an embossing roll 52 and a back up roll 53 for formation of the thickened densified portions 19. Roll 52 has a plurality of axially spaced, circumferentially extending rib-like projections 54 that bear upon the previously formed skin 51, and because of the residual mositure in the web and the increased pressure applied by projections 54, thickened densified portions 19 are produced.

The pressure applied by the projections 54 on the embossing roll also produces recesses 20 (FIG. 2) in alignment with thickened portions 19. As is evident from FIG. 2, the unthickened portions of the densified layer 18 merge with the loosely compacted batt 14 at a generally planar interface 21, and the thickened densified portions extend beyond interface 21 and into the loosely compacted batt 18 to give the absorbent panel a three dimensional strengthening effect.

In the absorbent web and in the batts cut therefrom, there are weak hydrogen bonds in the loosely compacted body of the batt providing sufficient strength to maintain the integrity of the batt in ordinary handling, and there are strong hydrogen bonds in the densified layer or skin to increase the cohesive strength of the composite. After the skin and the thickened portions are formed, the absorbent web comes into contact with a web of facing material 55 and is supported thereby while being cut by cutter 56 into individual batts 14. The facing material (previously prepared as described below) is fed from roll 57.

Polyethylene film 12 is fed to the assembly from roll 58, lines of adhesive being applied from applicator 59. As described above, the adhesive is applied as parallel lines or beads between the impervious sheet and the densified layer of the batt (or the facing layer in the marginal portion of the diaper). Adhesive may, if desired, be applied as a continuous layer between the polyethylene and the batt, but such application tends to provide excessive stiffness. The adhesive may also be applied in other patterns, such as spaced dots or other forms of so-called "island" bonds, but fairly close overall adhesion between the sheet and the batt is required and no portion of the polyethylene should be more than about 2 inches from a point of adhesion. In the absence of such close overall adhesion, the polyethylene film may be separated from the densified layer to create substantial spaces in which uncontrollably large amounts of free liquid urine can accumulate.

After the facing material and polyethylene are brought into contact with opposite faces of the absorbent batts, the assembly is subjected to compression by rolls 60 and 61 to shape the diaper assembly, and the individual diapers are cut off by cutter 62.

If desired, adhesive applicator 59 may be omitted and adhesion between the polyethylene layer and the fibrous layers may be achieved by heat sealing, employing a suitable sealing element in the production line.

The facing layer, as described above, contains between 75 percent and 98 percent by weight of short fibers, not exceeding about one-fourth inch in length. The average short fibers are from about one-sixteenth to about three-sixteenths inch in length. The facing layer is prepared by first forming a web of randomly laid dry fibers of the desired mix of short and long lengths, the web having a density from about 0.09 gm./cc. to about 0.025 gm/cc measured by ASTM Method D-1777 at 0.16 lbs./in.$^2$ Facing layers, as described above, having weights between about 1 and about 5 ounces per square yard are generally suitable for use in this invention. One particular facing layer which has been used with satisfaction is composed of approximately 15 percent textile-length fibers such as uniformly cut 1½ inch 1.5 denier rayon fibers and 85 percent fibers of individualized second cut cotton linters. This facing layer is made on a web laying device to a weight of 2 oz./yd.$^2$ This layer is then conveyed into a bonder including a suction means, and a bonding agent such as a self-cross-linking acrylic emulsion is applied. One bonding agent which has been employed with considerable success is a latex of a polyethyl-acrylate copolymer containing small amounts of acrylonitrile and a cross-linkage monomer sold under the trademark HYCAR 2600 × 120. The bonding agent should preferably be of the low viscosity type with a viscosity less than 5 centipoises.

To avoid excessive water repellency, a surfactant, preferably an anionic surfactant, is included in the binder suspension. A typical surfactant which has been found to be suitable is the ionic sulfonated alkyl ester sold under the trademark TRITON GR-5.

The composition of the binder suspension and the amount of suction at the suction slot is controlled in a typical application so as to give the fabric a dry solids add-on of 6 percent based on the fabric weight, of which about 0.15 percent is the amount of surfactant. A suitable range for the amount of binder is from about 4½ percent to about 9 percent, based on fabric weight.

The wet web is conveyed into a drying oven having a temperature of 310°-320°F., where it is dried and the resin binder cured. The resultant material has a density of 0.05 to 0.07 gm/cc., and a dry strength of about 1.4 lbs./in. of width in the cross direction. The wet strengths are about 0.9 lbs./in. of width in the machine direction and about 0.5 lbs./in. of width in the cross direction.

The bonding agent in the facing layer tends to provide the layer with greater dimensional stability than the body of the batt which contains no bonding agent. When the diaper is wet with urine and the infant's weight is on a portion thereof, both the facing layer and the body of the batt will be compressed under the weight, but the body of the batt is more subject to compression because it contains no bonding agent. This increased compaction in the body of the batt enhances the margin of wickability which it normally has in comparison to the facing layer (even when dry and uncompressed) and tends to hold the liquid strongly against migration into the facing layer where it could wet the infant's skin.

If desired, the facing layer may be made with a veneer of long fibers on one or both surfaces thereof, in place of or in addition to the long fibers intermixed with the short fibers.

In another embodiment, the facing layer may be made substantially entirely of textile length fibers bonded together with a resinous bonding agent. This embodiment can provide a facing layer of greater strength, but it is not preferred because it is more expensive and because the strength of the short fiber containing facing material is adequate in most instances.

In all embodiments of the invention, the adherence of the impervious layer to the densified layer, continuously or discontinuously, over substantially the entire interface between them is important because it prevents substantial separation between the two and the creation of substantial spaces in which substantial amounts of free liquid urine can accumulate. The adherence of the impervious layer to the paper-like densified cellulosic layer effects a dimensional stabilization of the densified layer against transverse movement and thereby brings about a stabilization of the loosely compacted fiber fluff portion of the batt layer since the paper-like densified layer is integral with the fluff portion of the batt, and holding forces are transmitted from the dimensionally stable impervious layer through the widely distributed adhesive, to the densified layer, and thence to the fluff.

Turning now to the embodiments of FIGS. 5-10, diaper structures are illustrated therein that are similar to the embodiment of FIGS. 1-3, so that similar reference numerals, increased by 100, have been used to designate those elements in FIGS. 5-11 which correspond with those in FIGS. 1-3.

As with the previous embodiment, the diaper assembly 110, when fully opened and laid out flat, comprises a lowermost water-impervious backing sheet 112 which is rectangular in shape, a highly water absorbent fibrous pad, or batt 114, which is also rectangular in shape, but slightly narrower than the impervious sheet 112 and centrally disposed thereon, and an overlying facing layer 116 of fibrous material, which is also rectangular in shape, equal in dimension, and coterminous with the impervious sheet and in contact therewith in the marginal portions of the diaper extending peripherally beyond the absorbent pad, i.e., in the portions 116b and 112b of facing layer 116 and impervious sheet 112, respectively. The batt 114, like batt 14, has a continuous paper-like densified highly compacted lowermost fibrous layer 118 that includes spaced, parallel thickened densified portions 119. Densified layer 118 is adhered to the impervious sheet by bead lines of adhesive 122 substantially throughout the interface therebetween. Marginal portions 116b and 112b are also adhered to each other by bead lines 122.

The embodiments of FIGS. 5-10 differ from the previously described embodiment in that the batt layer 114 of these embodiments is substantially wider than the batt layer 14, as can be observed by comparing FIGS. 1 and 5. For example, in the embodiment of FIGS. 1-3 the batt 14 is preferably spaced about 2¼ inches inwardly from the side marginal edges of facing layer 16; whereas in the embodiments of FIGS. 5-10, the batts 114 are preferably spaced about ½ inch to about 1 inch from the side marginal edges of the facing layer, and most preferably about three-fourths inch. As is evident from FIG. 5, even though batt layer 114 is only slightly narrower than facing layer 116 and backing sheet 112, the facing layer and backing sheet do extend beyond the marginal side portions of the batt, as noted above, although by a significantly lesser margin than in the embodiment of FIGS. 1-3.

Even though batt layer 114 is significantly wider than batt layer 14, in batt 114 essentially the same number of fibers may be utilized to provide a comparable absorbent capacity in a layer of approximately the same density. This results in batt layer 114 being somewhat thinner than batt layer 14, which has the added benefit that the diaper 110 is somewhat more conformable and easier to handle. This enables the sides of the diaper, when taped or pinned in place around the torso of an infant, to closely conform to the thighs of the infant with a minimum of wrinkling; which not only makes the diaper more comfortable to the infant, but which also makes the sealing around the infants thighs more efficient.

Since the batt layer 114 is thinner, the integral densified and selectively thickened layer 118 lends increased strength and stability to the batt layer, since the densified layer comprises a larger percentage of the cross-sectional thickness of the batt. The widened densified layer also provides a greater area for adherence to the backing sheet 112, so that the overall strength of the diaper is also improved.

Figure 8:
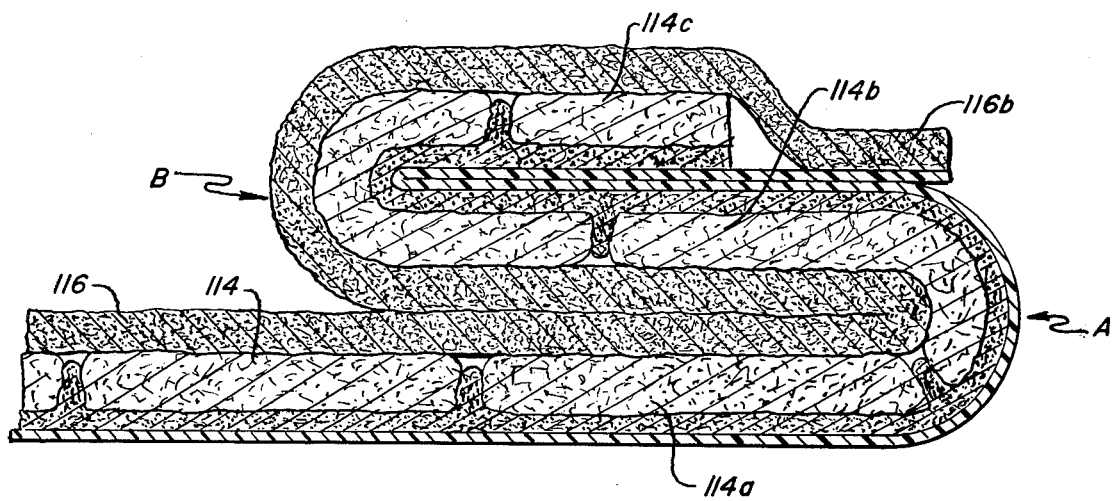
FIG. 8 is a partial cross section of the diaper in its final folded condition.
Figure 9:
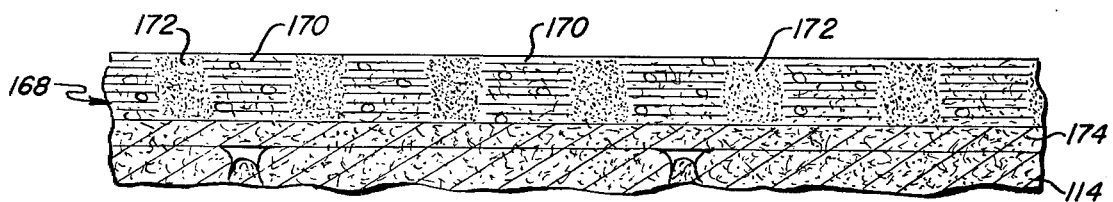
FIG. 9 is an enlarged partial cross section of a further diaper modification.

The diaper 110, when laid out flat, has the same lateral dimension as the diaper 10, so that when the diaper is folded into its final configuration for packaging, as shown in FIG. 8, the same apparatus heretofore utilized for folding the diaper 10 can also be used in connection with the diaper 110. Referring to FIG. 8, which shows the marginal side portion of the diaper folded inwardly about a first fold line A, and outwardly about a second fold line B, it will be noted that the batt layer 114 extends outwardly beyond both fold lines A and B, so that in the final folded configuration, three thicknesses (114a, 114b and 114c) are provided at each side of the diaper. The three thicknesses of batt material provide for increased bulk at opposite sides of the folded diaper, and when the diaper is secured around the torso of an infant, the increased bulk provides for improved sealing around the thighs of an infant in the crotch area.

As noted above, the wider but thinner batt 114 can provide a desired absorbent capacity within the batt, by virtue of utilizing substantially the same number of fibers. Thus, the improved sealing effects attributable to the three thicknesses of batt material at the sides of the diaper and the closer conformity with the infant's thighs are achieved with little or no increase in cost of the diaper itself. As also noted above, since the transverse dimension of diaper 110 is the same as the transverse dimension of diaper 10, essentially the same apparatus that was utilized to manufacture diaper 10 can be used to manufacture the diaper 110. The wider but thinner batt 114 may be provided by feeding a wider roll of compacted wood pulp 141 (FIG. 10) to a grinding mill 142 to provide a stream of fibers upon belt 143 in a manner similar to that described in connection with FIG. 4. The remainder of the apparatus, as previously noted, can be the same.

Figure 7:
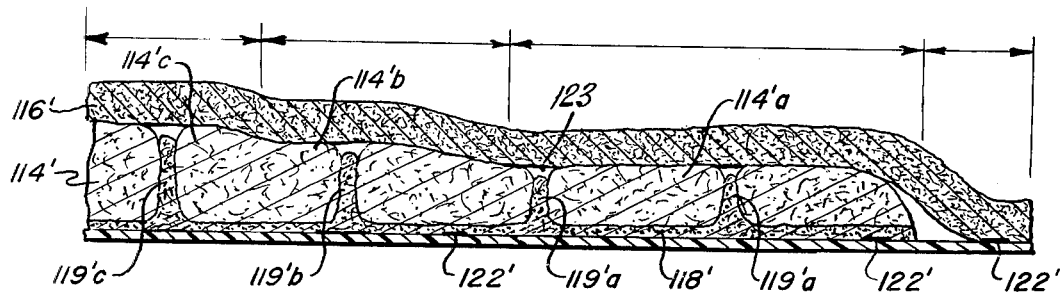
FIG. 7 is an enlarged partial cross section, similar to FIG. 6, and illustrating a further modification including a thickened central batt portion.

The thinner batt 114 also enables the diaper as a whole to have less abrupt changes in thickness, and therefore the diaper is more comfortable to the infant. In certain instances, as in a diaper intended for periods of heavy discharge, the batt may have an increased thickness in the center thereof. Referring to FIG. 7, the reference numerals used therein are the same as those used in FIG. 6 to designate common elements, with the reference numerals in FIG. 7 being primed. In the past, when it was desired to provide a diaper with an increased volumetric storage capacity, a separate layer of batt material was provided, as described in the above-mentioned patent. This diaper structure functioned satisfactorily for its intended purpose, and the diaper of the present invention represents an improvement thereon by eliminating the need for a separate element, while at the same time providing a more gradual transition between the unthickened and thickened portions of the batt.

It will be noted in FIG. 7 that the batt 114' has a stepped cross-sectional configuration including thin, lightweight marginal sections 114'a, somewhat thicker, somewhat heavier intermediate sections 114'b, and a thickest, heaviest central section 114'c. In a diaper wherein the facing and backing layers extend beyond the sides of the batt by about 3/4'', the batt sections 114'a may have a lateral dimension of about 3'', while the batt sections 114'b have a lateral dimension of about 1½'', and the batt section 114'c has a lateral dimension of about 2''. As is evident from FIG. 7, there is a smooth transition between batt sections 114'a and 114'b and between batt sections 114'b and 114'c, and the gradually stepped unitary construction of the batt improves the handle and feel of the diaper, particularly as compared to a diaper that is thickened in its central region by the use of a separate batt layer. The weight (i.e. lbs/in.$^2$) of central sections 114'c is preferably about twice that of side sections 114'a, while the weight of intermediate sections 114'b is preferably about 1½ times that of side sections 114'a. The contoured batt 114' is compressed during calendering to form the selectively thickened densified layer 118' (hereinafter described) so that the density of at least central section 114'c is increased relative to the density of side sections 114'a.

The batt arrangement illustrated in FIG. 7 may be provided by simultaneously feeding three rolls of wood pulp to a grinding mill. As shown in FIG. 11, roll 141 provides a first source of fibers, with roll 139, which is narrower than roll 141 and centrally disposed relative thereto, providing a second source of fibers, and with roll 140, which is narrower than roll 139 and centrally disposed relative thereto, provides a third source of fibers. The compacted wood pulp materials from rolls 139–141 may be simultaneously ground in mill 142 and deposited upon belt 143 to thereby produce the contoured and centrally thickened batt 114' shown in FIG. 7.

The selectively thickened densified layer 118' is formed as described above by moistening the deposited web, and subjecting the web to calendering and embossing pressure. With reference to FIG. 11, the web from belt 143 initially passes between compaction rolls 147, and a preselected quantity of moisture is applied to the surface of the web, as by nozzle 148. The web then passes between the nip of calendering rolls 149, and the present invention contemplates that the rolls 149 will be cylindrical in shape, even though the web has a stepped or contoured configuration. It has been found that by subjecting such a web to calendering pressure applied by cylindrical rolls, the densified layer 118' is thicker in the central region of the web than it is in the side margins thereof. By virtue of this construction, a larger volume of liquid can be retained in the central region of the diaper, as compared to a construction which includes a densified portion of uniform thickness.

The present invention also contemplates that the densified portion 118' which is thicker in its central region will also include a plurality of spaced, selectively further thickened portions, as in the previously described embodiments. To this end, while the surface of the batt is still moist, it is subjected to embossing pressure between an embossing roll 152 and a backup roll 153, with the embossing roll 152 having spaced ribs 154 thereon that produce longitudinally extending selectively thickened lines designated 119'a, 119'b and 119'c in FIG. 7. These spaced, selectively thickened densified portions preferably extend through a substantial portion of the cross sectional thickness of batt 114', and most preferably, these portions extend entirely through the cross-sectional thickness of the batt so as to be visible upon the surface of the batt opposite that including the continuous densified layer 118'. It should be noted that this latter feature is desirable in batts of uniform cross-sectional thickness, as well as in batts having a stepped construction as illustrated in FIG. 7. It should also be noted that in a batt having a stepped construction, the thicker densified portions 119'a are shorter than the thicker densified portions 119'b, which in turn are shorter than the thickened densified portions 119'c.

The upper portions, i.e. the portions adjacent facing 116', of such densified lines 119'a, 119'b and 119'c are spaced downwardly slightly from the upper surface of the batt to provide air gaps 123, which enhance the cushioning effect and overall feel of the diaper. Air gaps 123 are provided by virtue of the fact that embossing roll 152 is positioned beneath the batt, as compared to embossing roll 52, which is positioned above the batt, as is clear from FIG. 4. Embossing roll 152 is positioned closely adjacent to backup roll 153 to define a confined nip, whereat sufficient pressure is applied to the fibers on the unmoistened side of the batt to cause the moisture to wick through the entire cross-sectional thickness of the batt. Because of the pressure concentration between the smooth uncompressible surfaces of the ribs on the embossing roll and the facing surface of the backup roll, the upper ends of the thickened lines are given a density that is substantially the same as the density of the outer face of layer 118'. Since the fibers in the midportion of the thickened lines are compressed against one another, the density in the middle of the thickened lines is less than the density of the ends of the lines, or of the continuous skin 118', although the density of the middle of the lines is significantly greater than the density of the loosely compacted fluff portions adjacent the lines. The ribs 154 in the center of embossing roll 154 may have a reduced outer diameter, as compared to the ribs at the outer ends of the embossing roll, so that substantially uniform embossing pressure will be applied to the various portions of the batt.

In a batt construction which includes a continuous densified portion at one side thereof, with a plurality of spaced, selectively thickened further densified portions that extend completely through the cross-sectional thickness of the batt, a construction is produced which has significantly improved strength characteristics as compared to a batt having densified layers of uniform thickness, or even to a batt having a continuous densified layer that includes selectively thickened areas. The three dimensional strengthening effect attributable to the selectively thickened densified portion of increased height enables the remaining loosely compacted fluff portion of the batt to have a lower density than heretofore thought possible. In this regard, in the past in the production of batts of the type described herein the wood pulp starting material was premoistened prior to grinding, so that after the fibers were deposited in the form of a web and subjected to compaction, weak hydrogen bonds were formed in the loosely compacted batt portion to give the batt some degree of structural integrity. In producing batts wherein the selectively thickened densified portions extend either all the way through the cross-sectional thickness of the batt, or through a major portion of the cross-sectional thickness thereof, the step of premoistening the starting material is preferably eliminated entirely, so that the loosely compacted portion of the batt will be extremely light and fluffy. The overall density of the batt layer will be within the above mentioned range due to the presence of additional densified material within the densified lines of increased height, but the presence of the less dense loosely compacted portions makes the batt layer more comformable, and ultimately more comfortable to an infant when incorporated in a diaper. This improved property is obtained without sacrificing any volumetric storage capacity, since the batt layer can include approximately the same number of fibers as previously known comparable batts. In fact, diapers having a batt as desdribed above have been subjected to dunking tests, and have been found to have approximately the same volumetric storage capacity of diapers such as those illustrated in U.S. Pat. No. 3,613,055.

The thickened densified lines 119'a–119'c, in addition to strengthening the batt, also provide a mechanism for transporting a larger volume of fluid from an initially wetted area to remote areas of the densified layer 118', and in addition provide an increased storage capacity within the densified layer itself. As with the previously described embodiments, the portions of the densified layer 118' between the thickened lines 119'a–119'c function as bridging portions, so that liquid migrating outwardly from an initially wetted area encounters additional thickened lines which cause the liquid to rapidly spread longitudinally of the batt.

While the backing layers 112' and 112, and the facing layers 116' and 116 may be formed as described above in connection with the embodiments of FIGS. 1–3, the present invention also contemplates that specifically different facing layers may be utilized.

The facing layer may be an apertured nonwoven fabric formed, for example, in accordance with the teachings in commonly assigned U.S. Pat. Nos. 2,862,251; 3,081,514 and 3,081,515, the disclosures of which are expressly incorporated herein by this reference. Briefly, such fabrics are foraminous structures wherein groups or groupings of fibers have been rearranged from a fibrous nonwoven starting web into positions surrounding less dense fabric portions by passage of a fluid through the starting material. For example, with reference to FIG. 9, where a foraminous facing layer 168 is shown, the less dense foramina 170 are readily visible, as are the fiber groupings 172 therearound. The fibers within the groupings are mechanically interlocked, and may be arranged into various patterns, as is well understood by those skilled in the art. A suitable binder may be utilized to help retain the fibers in their rearranged locations, as is also well understood by those skilled in the art. The fabric can be made of naturally occurring fibers, synthetic fibers or blends thereof. Typical facing layers made of a polyester material may have a weight of three-fourths oz./yd.$^2$ In instances where the foramina are relatively large and particularly when the facing is formed of a polyester material, a layer 174 of tissue or the like may be interposed between facing layer 168 and batt 114 to prevent the short paper-making fibers to the batt from sifting through the facing.

It should be understood that the facing layer may be formed of nonapertured material, such as a nonwoven isotropic web, sponge, or the like.

The present invention also contemplates that the facing layer may be formed of a mixture of long and short fibers as described above, but with a non-ionic wetting agent being used to improve the wettability of the fabric. A typical surfactant that has been found to be particularly useful is a polyoxyethylene sorbitan monolaurate sold under the trademark TWEEN 20. In a typical application, where the binder suspension gives the fabric a dry solids add-on of 6 percent based on the fabric weight 0.30 is the amount of the surfactant.

In all of the aforementioned facings, the materials should be relatively hydrophobic so as to retard wicking within the facing layer.

Figure 12:
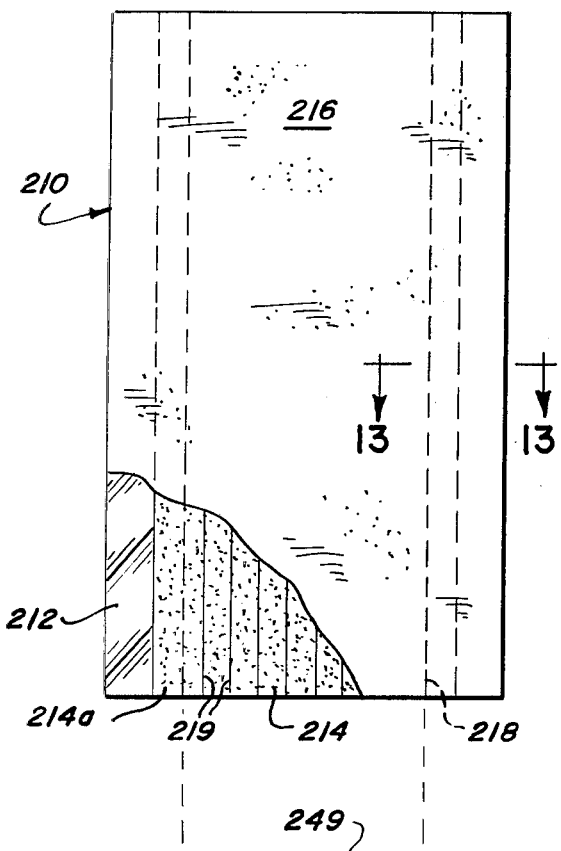
FIG. 12 is a top plan view, with certain portions broken away, of an open unfolded further embodiment of the diaper of the present invention.

Referring now to FIG. 12, a further diaper embodiment 210 is illustrated therein which is similar to the previous embodiments in that it includes a porous facing layer 216, which may take the form of any of the previously described facing layers; an absorbent panel or batt 214, as set forth above; and a moisture impervious sheet 212, also as described above. Like the previous embodiments, batt 214 is formed of loosely compacted short cellulose fibers, such as wood pulp fibers, or cotton linters, or mixtures thereof; with batt 214 including a continuous paper-like densified highly compacted lowermost fibrous layer or skin 218 that includes spaced parallel, thickened densified portions 219 which extend completely through the cross-sectional thickness of the batt, as in the embodiments of FIGS. 7–9. However, unlike the previously described embodiments, densified layer 218 does not completely cover the side of the batt that is positioned in engagement with backing sheet 212. Instead, the continuous densified layer 218 is limited to the central area of the batt, so that loosely compacted portions 214a are provided outwardly of the side marginal edges thereof. The loosely compacted strips 214a, which are of equal width and which extend from end to end of the batt 214 in the embodiment of FIG. 12, serve to slow up the spread of liquid, and minimize the possibility of liquid wicking beyond the sides of the batt.

Figure 12A:
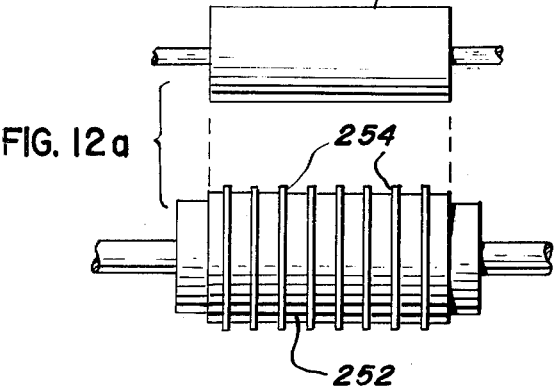
FIG. 12a is a side elevational view of rolls that are used in the manufacture of the embodiment of FIG. 12.
Figure 14A:
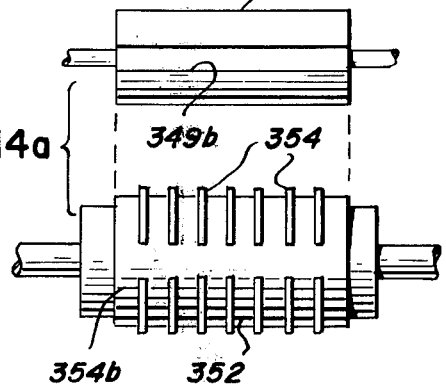
FIG. 14a is a side elevational view of a roll that is used in the manufacture of the embodiment of FIG. 13.

Densified layer 218 is formed in the manner described above, i.e., by moistening one side of the deposited layer of fibers and then serially subjecting the layer to calendering pressure to form the continuous densified layer and then to embossing pressure to form the thickened densified portions 219. With reference to FIG. 12a, a calendering roll 249 is shown therein which has a cylindrical configuration, and which has a length that is less than the width of batt 214. When the premoistened batt passes between roll 249 and a back up roll (not shown), the centralized continuous densified portion 218 is formed, and since so calendering pressure is applied to the side portions 214a of the batt, these portions remain loosely compacted. The batt layer, while still moist, then passes between an embossing roll 252 and a back up roll (not shown); andd spaced, circumferentially continuous ribs 254 on roll 252 form the thickened densified ribs or lines 219.

With the above described arrangement, where the calendering roll 249 and embossing roll 252 are narrower than the width of the batt 214, it is not critical to control the application of moisture to the batt and the entire surface of the batt can be moistened without having the densified portion 218 extend completely to the side marginal edges of the batt. However, if desired, moisture may be applied to only the central portion of the batt, in which case it is not critical to control the width of the calendering and embossing rolls.

Figure 14:
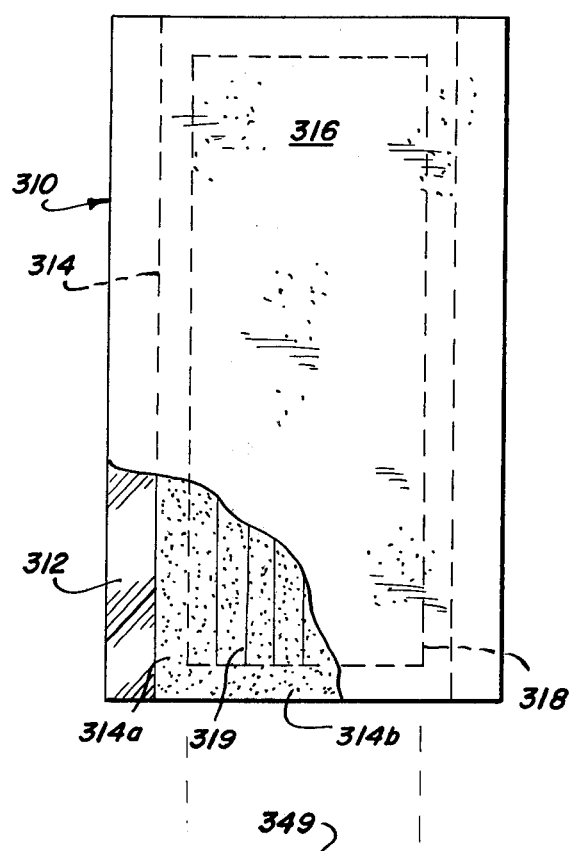
FIG. 14 is a top plan view similar to FIG. 12, and illustrating a still further embodiment of the invention.
Figure 13:
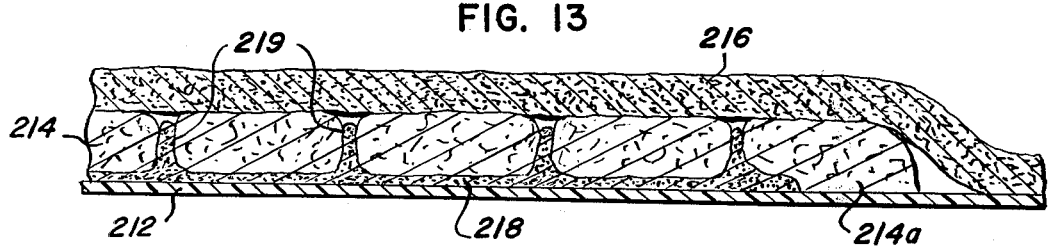
FIG. 13 is an enlarged partial cross section of the diaper of FIG. 12 taken along plane 13—13.

Referring now to FIG. 14, a still further diaper embodiment 310 is shown therein which is similar to the embodiment of FIGS. 12 and 13, so that similar reference numerals (increased by 100) have been used to designate the elements in FIG. 14 which correspond with those in FIGS. 12 and 13. The diaper 310 differs from the diaper 210 in that, in addition to having loosely compacted portions 314a outwardly of the sides of a central densified portion 318 on one side of the batt, batt 314 also has loosely compacted portions 314b outwardly of the ends of densified portion 318. This arrangement may be provided by subjecting the premoistened batt to embossing pressure between a back up roll (not shown) and an embossing roll 349 that is narrower than the batt and disposed centrally relative thereto, and which includes an axially extending portion 349b having a reduced diameter as compared to the remainder of the roll. Subsequent to calendering, the still moist batt layer passes between an embossing roll 352 and a back up roll (not shown) to form the thickened densified portions 319. As is clear from FIG. 14 a, ribs 354 are circumferentially discontinuous to provide a reduced diameter portion 354b which corresponds with reduced diameter portion 349b. It will be understood that when the diaper 310 is formed on an assembly line, such as that shown schematically in FIG. 11, the devce that severs the batt layer into individual batts is synchronized with calendering roll 349 and embossing roll 352 to cut the uncompacted batt portions left by reduced diameter roll portions 349b and 354b substantially medially thereof, so that the loosely compacted portions 314b at opposite ends of the batt are of substantially equal size.

It will be understood that with the arrangement described immediately above, loosely compacted batt portions 314a and 314b cooperate to provide substantially less dense zones that completely surround densified layer 318 and which effectively limit the likelihood of urine wicking beyond the edges of the densified layer of the batt and spreading into other areas of the diaper. In addition to being formed as described above, the present invention also contemplates that the limited densified layer 319 may be formed by moistening only the central area of the batt, and then applying calendering and embossing pressure thereto. It should also be noted that rolls 349 and 352 could be coextensive in length with the width of the batt, so that the densified layer would extend completely across the width of the batt, with loosely compacted portions 314b being present outwardly of each end of the densified layer.

While the thickened densified lines 19, 119, 219 and 319 in each of the previously described embodiments have been illustrated as being continuous in length, it should be understood that the present invention is not limited thereto, since the thickened lines may also be discontinuous and formed, for example, by a plurality of relatively closely spaced thickened strips or sections. While it is not desired to be limited to any specific dimensions, the thickened densified strips may be about 1½ inches long and separated from one another by about one-fourth inch. Most preferably, the thickened densified strips of adjacent lines are staggered relative to one another, so that the unthickened densified portions between the thickened strips are adjacent the midportions of the thickened strips of adjacent lines. Such discontinuous or intermittent thickened densified lines may be formed by subjecting a still moistened web having a continuous densified layer over a given area of one face thereof to embossing pressure applied by an embossing roll having a plurality of axially spaced ribs each defined by a plurality of circumferentially spaced rib segments that are adapted to form spaced thickened densified strips.

Diapers which include an absorbent panel having a continuous densified layer over a given area of one face thereof, with thickened intermittent or discontinuous lines formed therein, have been found to have improved feel and conformability, as compared to similar diapers having continuous thickened densified lines. The unthickened portions between the thickened strips provide less stiff zones, or in effect hinges, at a multiplicity of spaced locations within the diaper, to enable the diaper to be placed in close fitting conformity with the torso of an infant. Because of the improved inherent flexing capability of such a diaper, it is also more comfortable to the infant. Since the thickened densified strips are spaced relatively closely to one another, the strips of each line collectively cooperate to rapidly spread urine outwardly in the directions of the lines, so that the improved conformability and feel characteristics are provided with little or no loss in fluid directing properties. All of the thickened densified lines need not be discontinuous to provide the improved feel and conformability characteristics, and the present invention also contemplates that a combination of continuous and discontinuous thickened lines may be provided. Furthermore, the thickened densified strips of the discontinuous thickened lines, and the spacing between the thickened strips, need not be the same within each line, or in adjacent lines. It is desired that the thickened densified strips of the densified lines comprise from about 75% to about 95% of the total length of the lines.

The terms "thickened lines", "thickened regions" or "thickened portions", as used herein, are intended to refer to limited areas (as compared to the total area of the fibrous batt structure) in which at least some of the fibers above the continuous densified skin are more closely compacted than the fibers above the continuous densified skin in other areas of the fibrous batt structure, and the terms "thickened lines", "thickened regions" or "thickened portions" are meant to apply to both the coherent or unitary structures of FIGS. 1–14 and to structures having voids, pores, or gaps therein as shown in FIGS. 15–21. Within the areas designated as "thickened lines", "thickened regions" or "thickened portions", the densities (whether calculated on the basis of total volumes within these areas or on the basis of the volumes of the compacted portions without the voids) are higher than the density in other portions of the fibrous batt structure above the continuous densified skin. The "thickened lines", "thickened regions" or "thickened portions" as defined above can extend completely or partially through the cross-sectional thickness of the fibrous batt structure, it being understood that the amount of thickening is dependent upon the extent to which it is desired to rapidly transport fluid away from an initially wetted area and the degree to which it is desired to reinforce the fibrous batt structure.

Figure 15:
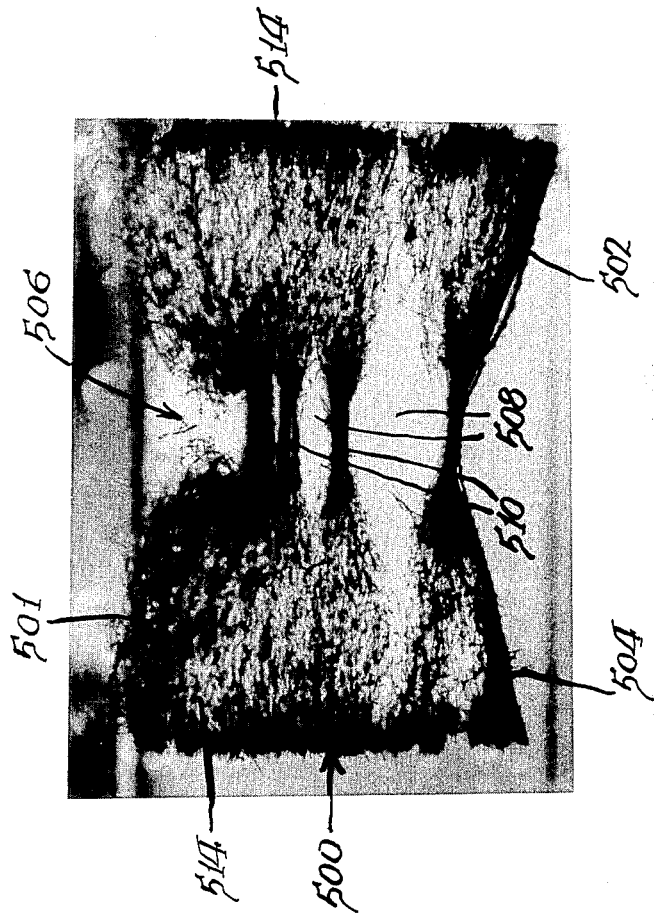
FIG. 15 is a photomicrograph of a cross section of a batt of yet another embodiment of the diaper of the present invention taken transversely to the length of the thickened line.
Figure 16:
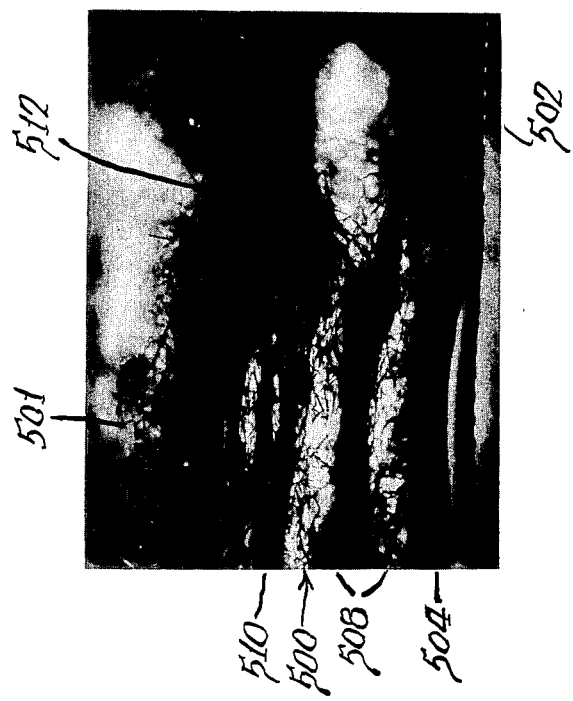
FIG. 16 is a photomicrograph of a batt as illustrated in FIG. 15 and taken in the direction of the thickened line.
Figure 18:
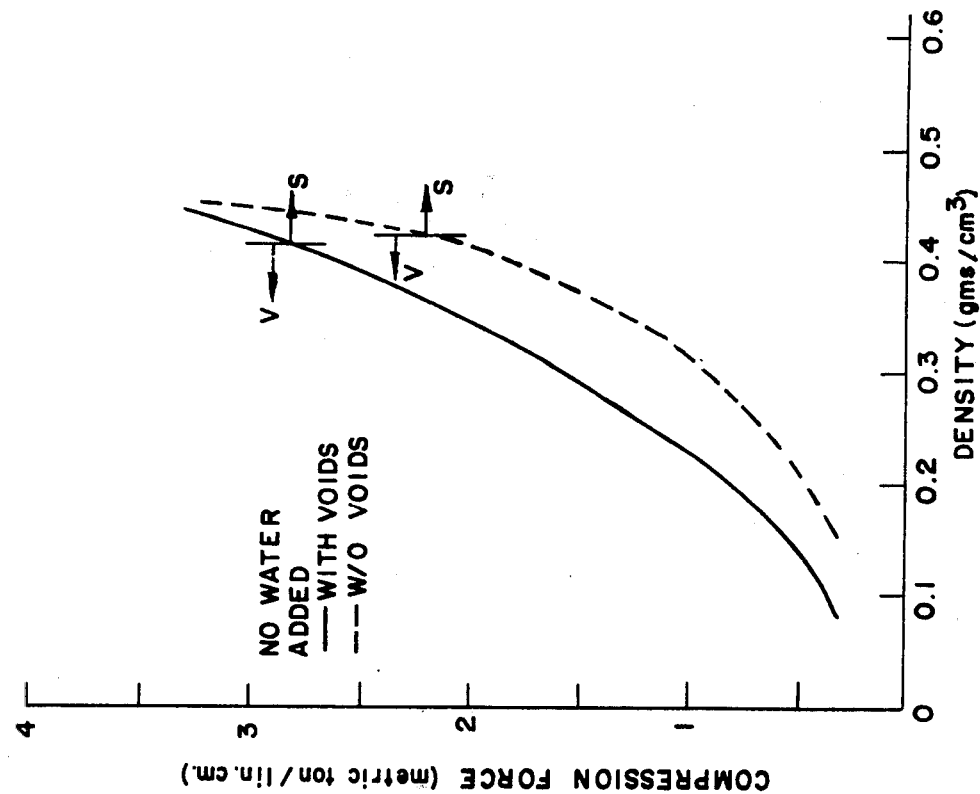

With specific reference to FIGS. 15 and 16, the disposable diaper illustrated in cross section therein is generally of the type shown in FIGS. 1–3, and includes a facing layer 501 of the type disclosed in U.S. Pat. No. 3,663,348, a batt 500 as hereafter described, and designated in its entirety by reference numeral 500, and attached to the batt backing sheet 502, which may be formed of a polyethelene film or other suitable film. As with the previous embodiments, batt 500 includes a loosely compacted cellulosic fibrous portion at the side thereof adjacent the facing layer, and integral therewith on the opposite side, a continuous paper-like densified, cellulosic fibrous layer 504. The upper portion of batt 500 is formed of loosely compacted short cellulose fibers, such as wood pulp fibers, or cotton linters, or mixtures thereof, which are primarily held together by interfiber bonds requiring no added adhesive, as is known in the art. The batt is a low bulk density coherent web of loosely compacted cellulose fibers preferably comminuted wood pulp fibers in the form of so-called "fluff".

Batt 500 is subjected to embossing pressure subsequent to the formation of the densified layer or skin 504 by a ribbed embossing roll, such as that shown at 54 in FIG. 4, to form a plurality of spaced, parallel thickened densified lines 506. However, unlike the previous embodiments, lines 506 are not coherent and unitary and instead, the moisture application and embossing forces are coordinated and controlled so that lines 506 have substantially fiber-free regions 508 therein, which may be termed "voids", "pores", "cells", "gaps", or "pockets".

As is evident by comparing FIGS. 15 and 16, lines 506 include a plurality of vertically spaced fiber-free regions 508 which are generally lens-shaped in transverse cross section (FIG. 15) and which are elongated in the direction of the lines (FIG. 16). The regions 508 are separated from one another by spaced fibrous strata 510 which are generally parallel with one another and with the opposite major faces of the batt 500, as can be best seen in FIG. 16. The strata 510 are of random or non-uniform length and merge together (and with the continuous densified portion 504) at longitudinally spaced locations 512 to completely enclose regions 508. As is also evident from FIGS. 15 and 16, regions 508 are of nonuniform cross-sectional dimension and length.

While it is not intended to be limited to any particular theory, it is believed that under certain selected moisture and pressure conditions (which may vary for different pulp fibers), as the batt dries subsequent to the embossing step, the hydrogen bonds which may have previously caused the lines to be cohesive or unitary begin to weaken due to the inherent recovery force of the fibrous mass, which cause the lines to separate as shown in FIGS. 15 and 16.

Batts such as shown in FIGS. 15 and 16 may also be produced by mechanically working a product having coherent or unitary lines, as by subjecting the product to bending and/or twisting forces, which cause certain of the hydrogen bonds to rupture, thus producing a product having thickened lines with dense fibrous strata surrounding substantially fiber-free regions.

While each of the strata 510 may have a density that is greater than the fibrous regions 514 at opposite sides of the lines 506, the density of the strata 510 is not necessarily uniform and the strata in the mid-portion of the batt may be less dense than the strata outwardly thereof.

It will be appreciated that with thickened densified lines having separated planes or strata of densified material, fluid will flow in the direction of the lines at a rapid linear rate, although the volumetric flow rate within each of the planes of densified material will, of necessity, be low because of the limited cross-sectional area in each plane. However, the voids or pores between the planes of densified material act as reservoirs into which excess liquid carried in the planes can be spilled, thereby providing an increased volumetric storage capacity and an increased volumetric carrying capacity, as compared to a cohesive or unitary line containing the same total amount of fibers.

Referring now to FIGS. 17–21, the graphs of these views illustrate the process conditions that are applicable to obtain thickened lines with or without voids for an NBF Kraft pulp available from Weyerhauser Company and which consists of approximately 80% Loblolly pine, 20% Ponderosa pine and traces of slash pine and which has a fiber classification of 54.6% + 12 mesh, 23.5% + 28 mesh, 10.8% + 48 mesh, 4.5% + 100 mesh, and 6.6% − 100 mesh. The pulp board was ground in a Fitz mill and processed as shown in FIG. 4. The embossing roll was floatingly mounted and loaded with a dead weight, and the embossing roll was formed of metal with a main diameter of 2.81 inches and a ring diameter of 2.94 inches, with a ring width of 0.125 inches. The back-up roll was formed of metal and was fixedly mounted relative to the embossing roll, with the backing roll having a diameter of 3,825 inches. For the purposes of FIGS. 17–20, void areas are those areas in excess of 0.05 m.m.

Figure 17:
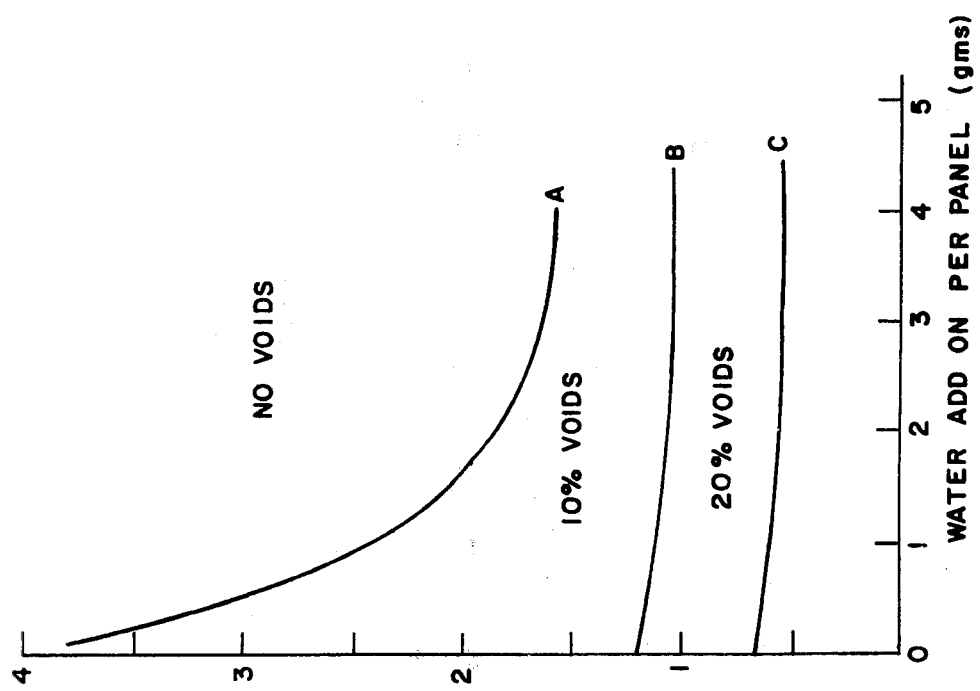
FIG. 17 is a graph illustrating the relationship between compression force and water add-on in connection with the embodiment illustrated in FIGS. 15 and 16.
Figure 21:
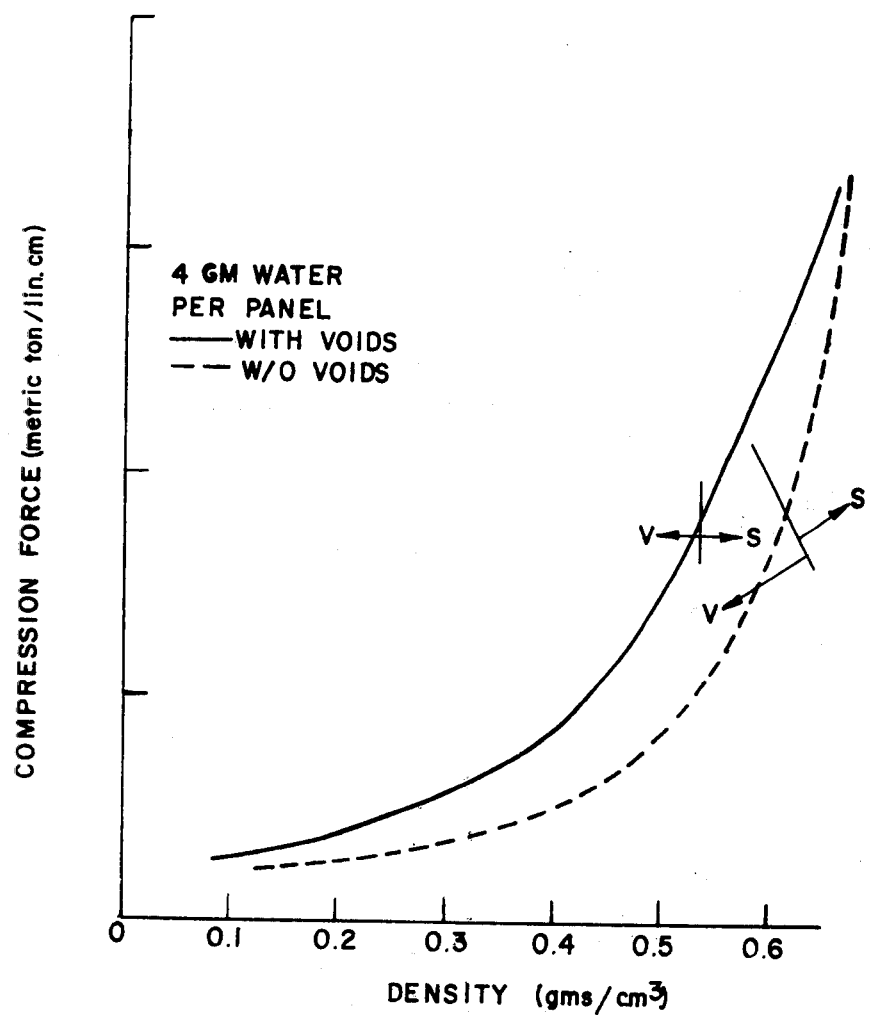

Referring first to FIG. 17, which is a plot with moisture add-on in increasing amounts as the abscissa and embossing force in increasing amounts as the ordinate, it should be noted that at those moisture and pressure conditions above line A, all of the thickened densified lines will be coherent and unitary, while at those moisture and pressure conditions below line A, the thickened densified lines will contain a percentage of regions substantially devoid of fibers. At increasing distances below line A, the percentage of samples having void regions increases, and above line B approximately 10% of the samples had void regions, while above line C approximately 20% of the samples had void regions. The samples that are graphed in FIG. 17 were taken immediately after production and at relatively low production speeds. Each sample below line A in FIG. 17 was observed to have void regions at given longitudinal sections thereof, and it is believed that void regions in up to 100% of the length of the densified lines of a given sample can be produced under certain process conditions including high-speed production runs where the time under pressure is short and the fibers have significant elastic recovery.

Turning now to FIGS. 18–21, which are plots with density in increasing amounts as the abscissa and embossing force in increasing amounts as the ordinate, the solid lines represent measurements that include the void regions, while the dotted lines represent measurements that exclude the void regions. The solid and dotted lines in each view represent [for moisture add-on per panel (10¾ inches × 14¾ inches of zero, 1 gram, 2 grams and 4 grams, respectively] lines of demarcation between those samples wherein the thickened densified lines had voids and those samples wherein the thickened densified lines were solid or coherent. In connection with FIG. 18, it should be noted that the fibers are not bone dry and that there is enough moisture in the ambient atmosphere to enable some hydrogen bonding to take place.

While processing conditions for obtaining structures as shown in FIGS. 15 and 16 have been given for only one specific type of fiber, it will be apparent to those skilled in the art that similar results can be obtained for different types of fibers, and that the specific reference to only one type of fibers is in no way meant to be limitative upon the invention.

It will be understood by those skilled in the art that variations and modifications of the specific embodiments described above may be employed without departing from the scope of the invention as defined in the appended claims.

What is claimed is:

1. A multi-layer diaper comprising: a porous facing layer in the form of a water-wettable bonded web of mixed long and short fibers; a highly porous, loosely compacted, cellulosic fibrous batt in face-to-face juxtaposition to said facing layer and having greater wettability to water than said facing layer; a paper-like, densified compacted cellulosic fibrous layer of relatively high wettability and relatively high fluid retentivity integral with said loosely compacted batt on the face thereof opposite the face in juxtaposition to said facing layer, said densified layer extending continuously over a given area of said batt and being of greater thickness dimension in selected regions, said regions of greater thickness dimension cooperating with the adjacent unthickened portions of said continuous densified layer to increase the fluid handling capacity of the densified layer and to direct the flow of fluid to selected areas of the densified layer, said regions of greater thickness dimension being integral with said densified layer and projecting into said loosely compacted batt to reinforce the same; and a water-impervious backing sheet adhered to said densified layer.

2. The diaper of claim 1 wherein said densified layer is of generally uniform thickness throughout a major portion of said given area and merges with said loosely compacted batt at a generally planar interface.

3. The diaper of claim 2 wherein the thickened regions of said densified layer extend beyond the plane of the interface between said batt and the continuous area of the densified layer and into said batt.

4. The diaper of claim 3 wherein the outer face of densified layer includes recesses in alignment with said thickened regions.

5. The diaper of claim 3 wherein the thickened regions of said densified layer are defined by relatively narrow zones spaced from and parallel with one another, and extending from end to end of said batt.

6. The diaper of claim 1 wherein said densified layer extends continuously over one entire side of said loosely compacted batt.

7. The diaper of claim 1 wherein said densified layer extends over a central area of one side of said loosely compacted batt to provide loosely compacted batt portions beyond the side edges of the densified layer area.

8. The diaper of claim 7 wherein said densified layer area extends from end to end of said one side of said loosely compacted batt.

9. The diaper of claim 7 wherein said densified layer area is spaced inwardly from the ends of said one side of said loosely compacted batt in addition to being spaced inwardly from the sides thereof.

10. The diaper of claim 1 wherein said backing sheet and said facing layer are substantially rectangular and substantially coextensive, said batt is substantially rectangular, narrower than said backing sheet and facing layer, and centrally disposed with respect thereto to provide marginal portions of said diaper in which said backing sheet and said facing web are in direct contact with each other.

11. The diaper of claim 1 wherein the selected thickened regions extend through a major portion of the cross-sectional thickness of the batt.

12. The diaper of claim 1 wherein the selected thickened regions extend through the entire cross-sectional thickness of the batt.

13. The diaper of claim 1 wherein the selectively thickened regions are provided by a plurality of spaced parallel lines, each line including a plurality of thickened strips separated by unthickened areas.

14. The diaper of claim 13 wherein the thickened strips are substantially longer than the unthickened areas.

15. A multi-layer diaper comprising: a porous facing layer in the form of a water-wettable bonded web of mixed long and short fibers, of which from about 75 to about 98 weight per cent are short fibers having a fiber length less than ¼ inch and from about 2 to about 25 weight per cent are long fibers having a fiber length between about ½ and about 2½ inches, said fibers being bonded together by a water-repellent bonding agent and coating with a surfactant; a highly porous, loosely compacted, cellulosic fibrous batt in face-to-face juxtaposition to said facing layer and having greater wettability to water than said facing layer; a paper-like, densified, compacted cellulosic fibrous layer of relatively high wettability and relatively high fluid retentivity integral with said loosely compacted batt on the face thereof opposite the face in juxtaposition to said facing layer, said densified layer extending continuously over a given area of said batt and being of generally uniform thickness throughout a major portion of said given area, said densified layer merging with said batt at a generally planar interface and including regions of greater thickness dimension than said major portion and extending beyond the plane of the interface and into said batt to reinforce the same, said regions of greater thickness dimension cooperating with the adjacent unthickened portions of said continuous densified layer to increase the fluid handling capacity of the densified layer and to direct the flow of fluid to selected areas of the densified layer, said regions of greater thickness dimension being integral with said densified layer; and a water-impervious backing sheet adhered to said densified layer by an adhesive discontinuously distributed over the entire interface between them, said backing sheet and facing layer being substantially rectangular and substantially coextensive and said batt being substantially rectangular, narrower than said backing sheet and facing layer and centrally disposed with respect thereto to provide marginal portions of said diaper in which said backing sheet and said facing layer are in direct contact with each other.

16. A multi-layer diaper comprising: a porous, facing layer adapted to be positioned adjacent an infant; a highly porous, loosely compacted, cellulosic fibrous batt positioned in face-to-face juxtaposition with said facing layer, the side edges of said batt terminating inwardly of the side edges of said facing layer, said batt being of unitary construction and the central portion thereof having a greater thickness dimension than the side portions thereof, whereby said batt has a stepped cross-sectional configuration; a water-impervious backing sheet positioned in face-to-face juxtaposition with said batt, said backing sheet being generally coextensive with said facing layer, and said facing layer and said backing sheet being adhered to one another in marginal areas beyond said batt, opposite side portions of said diaper being folded inwardly about first fold lines inwardly of the side edges of the batt, said side portions also being folded outwardly about second fold lines inwardly of the side edges of the batt and outwardly of the first fold lines to thereby provide thickened zones at opposite sides of the diaper that include three thicknesses of batt material; and a paper-like, densified compacted cellulosic fibrous layer of relatively high wettability and relatively high fluid retentivity integral with said loosely compacted batt on the face thereof that is positioned in juxtaposition with said backing sheet, said densified layer extending continuously over a given area of said batt and having an increased thickness dimension in selected regions, said regions of greater thickness dimension cooperating with the adjacent unthickened portions of said continuous densified layer to increase the fluid handling capacity of the densified layer and to direct the flow of fluid to selected areas thereof, said regions of greater thickness dimension being integral with said densified layer and projecting into said loosely compacted batt to reinforce the same.

17. The diaper of claim 16 wherein said densified layer extends over a central area of one side of said loosely compacted batt to provide loosely compacted batt portions beyond the side edges of the densified layer area.

18. The diaper of claim 16 wherein the selected thickened regions extend through a major portion of the cross-sectional thickness of the batt.

19. The diaper of claim 16 wherein the selected thickened regions extend through the entire cross-sectional thickness of the batt.

20. The diaper of claim 16 wherein the batt includes portions of intermediate thickness between the central and side portions of the batt.

21. The diaper of claim 16 wherein the densified layer is thickened in the central portion of the batt.

22. The diaper of claim 16 wherein said facing layer is a self-sustaining nonwoven foraminous structure formed of mechanically engaged groups of fibers.

23. A multi-layer diaper comprising: a porous facing layer adapted to be positioned adjacent an infant; a highly porous, loosely compacted, cellulosic fibrous batt in face-to-face juxtaposition to said facing layer and having greater wettability to water than said facing layer; a paper-like, densified compacted cellulosic fibrous layer of relatively high wettability and relatively high fluid retentivity integral with said loosely compacted batt on the face thereof opposite the face in juxtaposition to said facing layer, said densified layer extending continuously over a given area of said batt and being of greater thickness dimension in selected regions, said regions of greater thickness dimension cooperating with the adjacent unthickened portions of said continuous densified layer to increase the fluid handling capacity of the densified layer and to direct the flow of fluid to selected areas of the densified layer, said regions of greater thickness dimension being integral with said densified layer and projecting into said loosely compacted batt to reinforce the same; and a water-impervious backing sheet adhered to said densified layer.

24. The diaper of claim 23 wherein said facing layer is a self-sustaining nonwoven foraminous structure formed of mechanically engaged groups of fibers.

25. The diaper of claim 24 wherein a tissue layer is interposed between the facing layer and the batt.

26. The diaper of claim 23 wherein the selected thickened regions extend through a major portion of the cross-sectional thickness of the batt.

27. The diaper of claim 23 wherein the selected thickened regions extend through the entire cross-sectional thickness of the batt.

28. The diaper of claim 27 wherein the thickened regions of said densified layer are coherent and unitary.

29. The diaper of claim 27 wherein the thickened regions of said densified layer include spaced fibrous strata surrounding substantially fiber free voids.

30. The diaper of claim 29 wherein said voids are substantially lens-shaped in transverse cross section.

31. The diaper of claim 29 wherein said thickened regions include a plurality of vertically spaced voids separated by one another by vertically spaced strata.

32. The diaper of claim 29 wherein spaced portions of said strata merge with one another.

33. The diaper of claim 29 wherein the thickened regions of said densified layer are defined by relatively narrow zones spaced from and parallel with one another, and extending from end to end of said batt.

34. The diaper of claim 33 wherein said strata extend in the direction of said zones.

35. A multi-layer diaper comprising: a porous facing layer adapted to be positioned adjacent an infant; a highly porous, loosely compacted, cellulosic fibrous batt in face-to-face juxtaposition to said facing layer and having greater wettability to water than said facing layer, said batt being smaller than said facing layer and centered with respect thereto, the side margins of the facing layer extending beyond the sides of the batt by a distance of about ½ inch to about 1 inch, said batt being of unitary construction and having a central portion of greater thickness dimension than side portions thereof; a paper-like, densified compacted cellulosic fibrous layer of relatively high wettability and relatively high fluid retentivity integral with said loosely compacted batt on the face thereof opposite the face in juxtaposition to said facing layer, the central portion of said densified layer having an increased thickness dimension; and a water-impervious backing sheet adhered to said densified layer, said backing sheet being coterminous with said facing layer and secured thereto in the side margins thereof beyond said batt.

36. The diaper of claim 35 in which said densified layer extends continuously over a given area of said batt and includes a plurality of spaced, parallel regions of increased thickness dimension to increase the fluid handling capacity of the densified layer and to direct the flow of fluid to selected areas of the densified layer.

37. A multi-layer diaper comprising: a porous facing layer adapted to be positioned adjacent an infant; a highly porous, loosely compacted cellulosic fibrous batt in face-to-face juxtaposition to said facing layer and having greater wettability to water than said facing layer; a plurality of spaced, paper-like, densified compacted cellulosic regions of relatively high wettability and relatively high fluid retentivity integral with said loosely compacted batt, at least some of said densified regions extending through the entire cross-sectional thickness of the batt, so that paper-like zones are present on both major surfaces of said batt whereby said densified regions reinforce said batt; and a water-impervious backing sheet in face-to-face juxtaposition to said batt on the side thereof opposite from said facing layer.

38. The diaper of claim 37 wherein said batt includes a continuous densified layer on the side thereof adjacent said backing sheet, with said spaced densified regions being integral with said densified layer.

39. The diaper of claim 37 wherein said batt includes loosely compacted regions which extend through the entire cross-sectional thickness of the batt outwardly of at least some of said densified regions.

* * * * *

UNITED STATES PATENT AND TRADEMARK OFFICE
CERTIFICATE OF CORRECTION

PATENT NO. : 3,938,522
DATED : February 17, 1976
INVENTOR(S) : Repke, Virginia L.

It is certified that error appears in the above—identified patent and that said Letters Patent are hereby corrected as shown below:

In column 4, line 14, the word "stregthening" should read "strengthening".

In column 4, line 54, the word "stroage" should read "storage".

In column 4, line 61 the word "withou" should read "without".

In column 8, line 58, after "2%" -- to 25% -- should be inserted.

In column 8, line 63, the word "THe" should read "The".

In column 13, line 15, the word "HOwever" should read "However".

In column 20, line 27, the word " desdribed" should read "described".

In column 21, line 66, the word "andd" should read "and".

In column 26, line 1, "(10 3/4 inches X 14 3/4 inches" should read "(10 3/4 inches X 14 3/4 inches)".

In column 27, line 37, the word "coating" should read "coated".

Signed and Sealed this

Ninth Day of November 1976

[SEAL]

Attest:

RUTH C. MASON
*Attesting Officer*

C. MARSHALL DANN
*Commissioner of Patents and Trademarks*